(12) United States Patent
Croce et al.

(10) Patent No.: US 9,023,825 B2
(45) Date of Patent: May 5, 2015

(54) MATERIALS AND METHODS RELATED TO MODULATION OF MISMATCH REPAIR AND GENOMIC STABILITY BY MIR-155

(71) Applicant: The Ohio State University, Columbus, OH (US)

(72) Inventors: Carlo M. Croce, Columbus, OH (US); Nicola Valeri, Columbus, OH (US)

(73) Assignee: The Ohio State University, Columbus, OH (US)

( * ) Notice: Subject to any disclaimer, the term of this patent is extended or adjusted under 35 U.S.C. 154(b) by 0 days.

(21) Appl. No.: 14/284,706

(22) Filed: May 22, 2014

(65) Prior Publication Data

US 2014/0357697 A1  Dec. 4, 2014

Related U.S. Application Data

(62) Division of application No. 13/637,490, filed as application No. PCT/US2011/029348 on Mar. 22, 2011, now abandoned.

(60) Provisional application No. 61/318,042, filed on Mar. 26, 2010.

(51) Int. Cl.
*C12N 15/11* (2006.01)
*C12Q 1/68* (2006.01)
*C12N 15/113* (2010.01)

(52) U.S. Cl.
CPC .......... *C12N 15/113* (2013.01); *C12N 15/1137* (2013.01); *C12N 2310/113* (2013.01); *C12N 2310/3231* (2013.01); *C12N 2310/141* (2013.01)

(58) Field of Classification Search
None
See application file for complete search history.

*Primary Examiner* — Dana Shin
(74) *Attorney, Agent, or Firm* — MacMillan, Sobanski & Todd, LLC

(57) ABSTRACT

The present invention provides materials and methods related to modulation of mismatch repair and genomic stability by miR-155.

21 Claims, 10 Drawing Sheets
(10 of 10 Drawing Sheet(s) Filed in Color)

FIG. 8C　　　FIG. 8D

SEQUENCE LISTING

<160> NUMBER OF SEQ ID NOS: 25

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ggaacctgat tggattaccc                                              20

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ttataatcaa tccactgtgt ataaagg                                      27

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gaggtgaatt gggacgaaga                                              20

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ttataatcaa tccactgtgt ataaagg                                      27

<210> SEQ ID NO 5
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gcactgtggg atgtgttctt ctttatcaaa gtgtg                             35

<210> SEQ ID NO 6
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cacactttga taaagaagaa cacatcccac agtgc                             35

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 7
gaggtgaatt gggacgaaga                                          20

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 8
ttataatcaa tccactgtgt ataaagg                                  27

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 9
cagaaagccc tggaacttga                                          20

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 10
tcaattgcaa acagtcctca g                                        21

<210> SEQ ID NO 11
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 11
atattgtttt atattctgtc agtgcccatg ggc                           33

<210> SEQ ID NO 12
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 12
gcccatgggc actgacagaa tataaaacaa tat                           33

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
aaatgttgct gtgcgccta                                                19

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ccacctttgt cagaagtcaa ctc                                           23

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gcttgctaat ctcccagagg                                               20

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ccacctttgt cagaagtcaa ctc                                           23

<210> SEQ ID NO 17
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ggaagggaac ctgattggat ctatgtgccc cctttggagg g                       41

<210> SEQ ID NO 18
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ccctccaaag ggggcacata gatccaatca ggttcccttc c                       41

-continued

```
<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ctcaaaatgt tgctgtggca tgcatggtag                                     30

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ctaccatgca tgccacagca acattttgag                                     30

<210> SEQ ID NO 21
<211> LENGTH: 19
<212> TYPE: RNA
<213> ORGANISM: Homo sapiens

<400> SEQUENCE: 21
uaccccuucu gauugacaa                                                 19

<210> SEQ ID NO 22
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
uuaaugcuaa ucgugauagg ggu                                            23

<210> SEQ ID NO 23
<211> LENGTH: 28
<212> TYPE: RNA
<213> ORGANISM: Homo sapiens

<400> SEQUENCE: 23
uucucuguau uccgauacaa aguguugu                                       28

<210> SEQ ID NO 24
<211> LENGTH: 22
<212> TYPE: RNA
<213> ORGANISM: Homo sapiens

<400> SEQUENCE: 24
aacccuuuuu ccauaguguu aa                                             22

<210> SEQ ID NO 25
<211> LENGTH: 22
<212> TYPE: RNA
<213> ORGANISM: Homo sapiens

<400> SEQUENCE: 25
ugcgccuagg acauauggca ug                                             22
```

MATERIALS AND METHODS RELATED TO MODULATION OF MISMATCH REPAIR AND GENOMIC STABILITY BY MIR-155

CROSS-REFERENCE TO RELATED APPLICATIONS

This application is filed under 35 U.S.C §121 as a divisional application claiming the benefit under 35 U.S.C. §120 of U.S. application Ser. No. 13/637,490, filed under 35 U.S.C. §371 on Dec. 4, 2012, published; which is the national phase entry of international patent application PCT/US2011/029348, filed under the authority of the Patent Cooperation Treaty on Mar. 22, 2011, published; which claims priority to U.S. Provisional Application No. 61/318,042, filed under 35 U.S.C. §111(b) on Mar. 26, 2010. The entire disclosure of each priority document is expressly incorporated herein by reference.

STATEMENT REGARDING FEDERALLY SPONSORED RESEARCH

This invention was made with government support under Grant Numbers GM080176, CA067007, CA124541, and CA135030, awarded by the National Institutes of Health. The government has certain rights in this invention.

SEQUENCE LISTING

The instant application contains a Sequence Listing which has been submitted via EFS-web and is hereby incorporated by reference in its entirety. The ASCII copy, created on Mar. 21, 2011, is named 604_51754_SEQ_LIST_OSU-10126.txt, and is 5,627 bytes in size.

TECHNICAL FIELD

This invention relates generally to the field of molecular biology. More particularly, it concerns cancer-related technology. Certain aspects of the invention include application in diagnostics, therapeutics, and prognostics of miR-155 associated disorders.

BACKGROUND OF THE INVENTION

Mismatched nucleotides may arise from polymerase misincorporation errors, recombination between heteroallelic parental chromosomes, or chemical and physical damage of the DNA. MutS homologs (MSH) and MutL homologs (MLH/PMS) are highly conserved proteins and are essential for the MMR excision reaction. In human cells, hMSH2 and hMLH1 are the fundamental components of MMR. The hMSH2 protein forms a heterodimer with hMSH3 or hMSH6 and is required for mismatch/lesion recognition, while the hMLH1 protein forms a heterodimer with hMLH3 or hPMS2 and forms a ternary complex with MSH heterodimers to complete the excision repair reaction. Human cells contain at least 10-times more of the hMSH2-hMSH6/hMLH1-hPMS2 complex, that repairs single nucleotide and small insertion-deletion loop (IDL) mismatches, than the hMSH2-hMSH3/hMLH1-hMLH3 complex that repairs primarily large IDL mismatches. In addition to MMR, the hMSH2-hMSH6/hMLH1-hPMS2 components have been uniquely shown to recognize lesions in DNA and signal cell cycle arrest and apoptosis.

Mutations in the hMSH2, hMSH6, hMLH1 and hPMS2 core MMR genes have been linked to LS/HNPCC. These observations have provided considerable support for the Mutator Hypothesis since defects in the MSH and MLH/PMS genes significantly increase cellular mutation rates that may then drive the evolution of numerous oncogene and tumor suppressor gene mutations found in cancer. One signature of a mutator phenotype is instability of simple repeat sequences or microsatellite DNA (microsatellite instability or MSI). Virtually all LS/HNPCC tumors display MSI that is a result of mutation or inherited epigenetic inactivation of the core MMR genes). The majority of the 10-40% of sporadic CRC, endometrial, ovarian, gastric and urothelial tumors that display MSI are a result of acquired hMLH1 promoter methylation. Approximately 95% of MSI tumors can be at least partially accounted by mutation and/or epigenetic inactivation of the core MMR components. The remaining 5% as well as a significant proportion of the biallelic MMR inactivation mechanism remain poorly understood.

MicroRNAs (miR) are non-coding RNAs that play a role in the post-transcriptional regulation of more than 30% of human genes controlling critical biological processes, including development, cell differentiation, apoptosis and proliferation. Over-expression of miR155 has been observed in CRC, and appears more frequent MSI CRC compared to microsatellite stable (MSS) tumors.

There is no admission that the background references disclosed in this section legally constitutes prior art.

In spite of considerable research into diseases associated with MMR dysfunction, they remain difficult to diagnose and treat effectively, and the mortality observed in patients indicates that improvements are needed in the diagnosis, treatment and prevention of these diseases.

SUMMARY OF THE INVENTION

The present invention is based on the following information and discoveries: Inactivation of mismatch repair (MMR) is the cause of the common cancer predisposition disorder Lynch Syndrome (LS; or hereditary non-polyposis colorectal cancer, HNPCC) as well as 10-40% of sporadic colorectal, endometrial, ovarian, gastric, and urothelial cancers. Elevated mutation rates (mutator phenotype) including simple repeat instability (microsatellite instability or MSI) are a signature of MMR defects. MicroRNAs (miR5) have been implicated in the control of critical cellular pathways involved in development and cancer. Here the inventors show that overexpression of miR-155 significantly down-regulates the core MMR proteins, hMSH2, hMSH6, and hMLH1, inducing a mutator phenotype and MSI. An inverse correlation between the expression of miR-155 and the expression of MLH1 or MSH2 proteins was found in human colorectal cancers (CRC). Finally, a number of MSI tumors with unknown cause of MMR inactivation display miR-155 over-expression. These data provide support for miR-155 modulation of MMR as a new mechanism of cancer pathogenesis.

Various objects and advantages of this invention will become apparent to those skilled in the art from the following detailed description of the preferred embodiment, when read in light of the accompanying drawings.

The present invention provides compositions of matter comprising at least one anti-sense miRNA and at least one additional composition, wherein the anti-sense miRNA is anti-sense to an miRNA that is capable of downregulating at least one core MMR protein, and wherein the at least one additional composition is useful to treat MMR-related disease. Preferably, the at least one additional composition is selected from the group consisting of: a chemotherapy drug; a stem cell; AG1478; gefitinib (Iressa®); erlotinib (Tarceva®); cetuximab; panitumab; zalutumamab; nimotuzamab; matuzumab; and lapatinib. Preferably, the antisense miRNA is miRNA-155, and/or wherein the at least one core MMR protein is selected from the group consisting of: hMSH2; hMSH6; and hMLH1.

Also provided are methods to identify MMR dysfunctional cells in a test sample, comprising comparing miRNA-155 levels in a test sample to miRNA-155 levels of a control, wherein differentially-expressed miRNA-155 levels identify the test sample as containing MMR dysfunctional cells.

Also provided are methods of diagnosing whether a subject has, or is at risk for developing, MMR mutant cells, comprising comparing miRNA-155 levels in a test sample to miRNA-155 levels of a control, wherein differentially-expressed miRNA-155 levels diagnoses the subject as either having, or being at risk for developing, MMR mutant cells.

Also provided are methods of diagnosing whether a subject has, or is at risk for developing, Lynch Syndrome, comprising comparing miRNA-155 levels in a test sample to miRNA-155 levels of a control, wherein differentially-expressed miRNA-155 levels diagnoses the subject as either having, or being at risk for developing, Lynch Syndrome.

Also provided are methods of diagnosing whether a subject has, or is at risk for developing, hereditary nonpolyposis colorectal cancer, comprising comparing miRNA-155 levels in a test sample to miRNA-155 levels of a control, wherein differentially-expressed miRNA-155 levels diagnoses the subject as either having, or being at risk for developing, hereditary nonpolyposis colorectal cancer.

Also provided are methods of diagnosing whether a subject has, or is at risk for developing cancer, comprising comparing miRNA-155 levels in a test sample to miRNA-155 levels of a control, wherein differentially-expressed miRNA-155 levels diagnoses the subject as either having, or being at risk for developing, cancer, wherein the cancer is selected from the group consisting of: colorectal; endometrial; ovarian; gastric; and urothelial.

Also provided are methods to provide a prognosis in a patient, comprising: comprising comparing miRNA-155 levels in a test sample to miRNA-155 levels of a control, wherein downregulated miRNA-155 levels indicates a poor prognosis.

Also provided are methods to treat MMR dysfunction in patient in need of such treatment, comprising administering a pharmaceutically-effective amount of a composition herein. Preferred are those methods wherein the MMR dysfunction is selected from the group consisting of: neuroblastoma; lung cancer; bile duct cancer; non small cell lung carcinoma; hepatocellular carcinoma; lymphoma; nasopharyngeal carcinoma; ovarian cancer; head and neck squamous cell carcinoma; squamous cell cervical carcinoma; gastric cancer; colon cancer; uterine cervical carcinoma; gall bladder cancer; prostate cancer; breast cancer; testicular germ cell tumors; large cell lymphoma; follicular lymphoma; colorectal cancer; malignant pleural mesothelioma; glioma; thyroid cancer; basal cell carcinoma; T cell lymphoma; t(8;17)-prolyphocytic leukemia; myelodysplastic syndrome; pancreatic cancer; t(5;14)(q35.1;q32.2) leukemia; malignant fibrous histiocytoma; gastrointestinal stromal tumor; and hepatoblastoma. Also preferred are those methods wherein the cancer treated is selected from the group consisting of: colorectal; endometrial; ovarian; gastric; and urothelial.

Also provided are methods to treat cancer in a MMR dysfunctional patient in need of such treatment, comprising administering a pharmaceutically-effective amount of an anti-sense miRNA, wherein the antisense miRNA is antisense to miRNA-155. Preferred are those methods wherein the cancer treated is selected from the group consisting of: colorectal; endometrial; ovarian; gastric; and urothelial. Also preferred are those methods which further comprise administering an adjuvant. More preferred are those methods which further comprises administering a compound selected from the group consisting of: compound selected from the group consisting of: a chemotherapy drug; a stem cell; AG1478; gefitinib (Iressa®); erlotinib (Tarceva®); cetuximab; panitumab; zalutumamab; nimotuzamab; matuzumab; and lapatinib.

Also provided are methods for inducing apoptosis of MMR dysfunctional cells, comprising introducing an apoptosis-effective amount of a composition as described herein.

Also provided are methods for inducing apoptosis of MMR dysfunctional cells, comprising introducing an apoptosis-effective amount of an anti-sense miRNA, wherein the anti-sense miRNA is antisense to miR-155. Preferred are those methods wherein cells are dysfunctional due to at least one downregulated core MMR protein, the protein selected from the group consisting of: hMSH2; hMSH6; and hMLH1. Also preferred are those methods wherein the cells are dysfunctional due to microsatellite instability. Also preferred are those methods which further comprises introducing a compound selected from the group consisting of: a chemotherapy drug; a stem cell; AG1478; gefitinib (Iressa®); erlotinib (Tarceva®); cetuximab; panitumab; zalutumamab; nimotuzamab; matuzumab; and lapatinib.

Also provided are methods for identifying pharmaceutically-useful compositions, comprising: introducing an anti-sense miRNA-155 to MMR dysfunctional cell culture; introducing a test composition to MMR dysfunctional cell culture; and identifying test compositions which induce apoptosis as pharmaceutically-useful compositions.

Also provided are methods of predicting the clinical outcome of a patient diagnosed with an MMR dysfunction disease, comprising detecting the expression level of miR-155 in a MMR dysfunction disease cell sample obtained from the patient, wherein a 1.5-fold or greater increase in the level of miR-155 relative to a control, in combination with a MMR dysfunction status predicts a decrease in survival.

Also provided are methods to identify a therapeutic agent for the treatment of MMR dysfunction disease, comprising screening candidate agents in vitro to select an agent that decreases expression of miR-155, thereby identifying an agent for the treatment of MMR dysfunction disease.

Also provided are kits for identifying a differentially-expressed miR-155 in MMR dysfunction disease, comprising at least one molecular identifier of miR-155.

Also provided are kits for identifying a differentially-expressed miR-155 in lung cancer, comprising at least one molecular identifier of miR-155, wherein said molecular identifier is selected from the group consisting of: probes; primers; antibodies; or small molecule.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the Patent Office upon request and payment of the necessary fee.

FIG. 1A: Location of the target sites of miR-155 in the 3'UTRs and/or the CDS of the indicated genes is shown (see also FIG. 6). Base position is counted from the first nucleotide in the CDS.

FIG. 1B: Colo-320 DM cells were transfected with the phRL-SV40 construct as control and either the luciferase construct WT or MUT-155 and with pre-miR-155 or pre-miR control. After 24 h, dual luciferase assays were performed. * p<0.005 relative to pre-miR control.

FIG. 2A: Transfection efficiency was confirmed by real time PCR. miR-155 expression was normalized to that of RNU44. Error bars represent S.E.M. * p<0.001 (N=3).

FIG. 2B: miR-155 exerts a post-transcriptional effect on MMR core proteins. mRNA expression of indicated genes was normalized to that of vinculin. Error bars represent S.E.M.* p<0.05 compared to control pre-miR (N=3).

FIG. 2C: A representative blot of western blotting analysis along with the mean and S.E.M. of 3 independent experiments are shown.* p<0.005 compared to control pre-miR.

FIG. 3A: Representative Western analysis along with mean and S.E.M. of 3 independent experiments are shown. * p<0.05 relative to controls.

FIG. 3B: mRNA expression of selected genes assessed by real time PCR (normalized to vinculin). Error bars represent S.E.M. * p<0.05 (N=3).

FIG. 3C: miR-155 expression was assessed by Northern analysis (MV-411 cells used as positive controls).

FIG. 3D: Microsatellite analysis of Colo-155 and Coloempty cells using the BAT-26 and BAT 25 (mononucleotide repeats) and D175250 (dinucleotide repeat) markers. Size markers are shown on top.

FIG. 4A: Paraffin-embedded, formalin-fixed CRC tissues were incubated with LNA-probe anti-miR-155 or scrambled probe and IHC antibodies against MSH2 and MLH1. Representative photographs were captured with the Nuance system software with staining positive for both miR-155 and MSH2 or MLH1 shown. Blue and red staining identifies miR-155 and the target protein respectively. Co-localization of miR-155 and the MLH1 or MSH2 in the same cell nest is not observed.

FIG. 4B: RNA and proteins extracted from fresh frozen human colorectal tissues. miR-155 expression was assessed by real time PCR, and MMR proteins expression by Western analysis. CRC with up-regulation (>2 fold) of miR-155 expression and down-regulation of MMR protein expression are shown. A strong correlation between loss of hMLH1 and hMSH2 expression and miR-155 expression increased above a 3-fold in tumor compared to adjacent normal tissue was observed (red line). Samples with miR-155 cancer/normal ratio below 3-fold displayed an uncertain effect on MMR expression.

FIG. 5A: CR-78 cancer tissue (with unknown causes of MLH1 loss) shows strong miR-155 expression (large arrow), while stroma (small arrow) is negative for miR-155 expression.

FIG. 5B: CR-79 tissue (MLH1 loss due to promoter methylation) shows faint expression of miR-155 only in inflammatory cells (large arrow). No signal is detected in cancer tissue (small arrow).

FIGS. 8A-8D: Inhibition of miR-155 increases the expression of MMR proteins. MV4-11 cells have been transfected with anti-miR-155 or anti-miR control for 48 hours (FIG. 8A) expression of miR-155 assessed by real time PCR (normalized to RNU6). Bars represent mean and S.E.M. of 3 replicates. * P: 0.003.

FIG. 8B: Evaluation of miR-155 by northern blotting analysis.

FIG. 8C: Cell lysates were obtained after 48 hours of transfection and immunoblotted with indicated antibodies. Representative blots are shown along with quantization of 3 experiments are shown. * p<0.005

FIG. 8D: Graph showing protein expression, relative to control for MLH1, MSH2, MSH6, for anti-miR-control and anti-miR-155.

FIG. 9A: Inflammatory cirrhotic tissue with positive staining for miR-155 was used as positive control.

FIG. 9D: Graphic representation of the proportion of cases with positive or negative staining for miR-155 and MLH1 or MSH2 are shown.

DETAILED DESCRIPTION

Figure 1A:
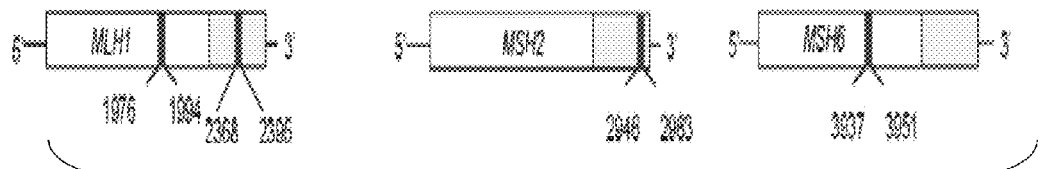
FIGS. 1A-1B: hMLH1, hMSH2 and hMSH6 are direct targets of miR-155.

The present invention therefore provides materials and methods related to these new discoveries. In particular, compositions useful to treat such disorders as described herein, and as would be known to those skilled in the art. Also provided are methods to identify additional compositions useful to treat, methods to diagnose, methods to provide prognosis, methods to induce apoptosis, etc. Also provided are research tools associated with these discoveries, particularly kits and the like.

DEFINITIONS

DNA Deoxyribonucleic acid
mRNA Messenger RNA
PCR Polymerase chain reaction
pre-miRNA Precursor microRNA
qRT-PCR Quantitative reverse transcriptase polymerase chain reaction
RNA Ribonucleic acid It is to be understood that both the foregoing general description and the following detailed description are exemplary and explanatory only and are not intended to limit the scope of the current teachings. In this application, the use of the singular includes the plural unless specifically stated otherwise.

The use of the word "a" or "an" when used in conjunction with the term "comprising" in the claims and/or the specification may mean "one," but it is also consistent with the meaning of "one or more," "at least one," and "one or more than one."

Also, the use of "comprise", "contain", and "include", or modifications of those root words, for example but not limited to, "comprises", "contained", and "including", are not intended to be limiting. The term "and/or" means that the terms before and after can be taken together or separately. For illustration purposes, but not as a limitation, "X and/or Y" can mean "X" or "Y" or "X and Y".

It is understood that an miRNA is derived from genomic sequences or a gene. In this respect, the term "gene" is used for simplicity to refer to the genomic sequence encoding the precursor miRNA for a given miRNA. However, embodiments of the invention may involve genomic sequences of a miRNA that are involved in its expression, such as a promoter or other regulatory sequences.

The term "miRNA" generally refers to a single-stranded molecule, but in specific embodiments, molecules implemented in the invention will also encompass a region or an additional strand that is partially (between 10 and 50% complementary across length of strand), substantially (greater than 50% but less than 100% complementary across length of strand) or fully complementary to another region of the same single-stranded molecule or to another nucleic acid. Thus, nucleic acids may encompass a molecule that comprises one or more complementary or self-complementary strand(s) or "complement(s)" of a particular sequence comprising a molecule. For example, precursor miRNA may have a self-complementary region, which is up to 100% complementary miRNA probes of the invention can be or be at least 60, 65, 70, 75, 80, 85, 90, 95, or 100% complementary to their target.

The term "combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, ACB, CBA, BCA, BAC, or CAB.

Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

In order to facilitate review of the various embodiments of the disclosure, the following explanations of specific terms are provided:

Adjunctive therapy: A treatment used in combination with a primary treatment to improve the effects of the primary treatment.

Clinical outcome: Refers to the health status of a patient following treatment for a disease or disorder or in the absence of treatment. Clinical outcomes include, but are not limited to, an increase in the length of time until death, a decrease in the length of time until death, an increase in the chance of survival, an increase in the risk of death, survival, disease-free survival, chronic disease, metastasis, advanced or aggressive disease, disease recurrence, death, and favorable or poor response to therapy.

Control: A "control" refers to a sample or standard used for comparison with an experimental sample, such as a tumor sample obtained from a patient.

Cytokines: Proteins produced by a wide variety of hematopoietic and non-hematopoietic cells that affect the behavior of other cells. Cytokines are important for both the innate and adaptive immune responses.

Decrease in survival: As used herein, "decrease in survival" refers to a decrease in the length of time before death of a patient, or an increase in the risk of death for the patient.

Detecting level of expression: For example, "detecting the level of miR or miRNA expression" refers to quantifying the amount of miR or miRNA present in a sample. Detecting expression of the specific miR, or any microRNA, can be achieved using any method known in the art or described herein, such as by qRT-PCR. Detecting expression of miR includes detecting expression of either a mature form of miRNA or a precursor form that is correlated with miRNA expression. Typically, miRNA detection methods involve sequence specific detection, such as by RT-PCR. miR-specific primers and probes can be designed using the precursor and mature miR nucleic acid sequences, which are known in the art and provided herein as in the SEQ ID NOs.

MicroRNA (miRNA): Single-stranded RNA molecules that regulate gene expression. MicroRNAs are generally 21-23 nucleotides in length. MicroRNAs are processed from primary transcripts known as pri-miRNA to short stem-loop structures called precursor (pre)-miRNA and finally to functional, mature microRNA. Mature microRNA molecules are partially-complementary to one or more messenger RNA molecules, and their primary function is to down-regulate gene expression. MicroRNAs regulate gene expression through the RNAi pathway.

miR expression: As used herein, "low miR expression" and "high miR expression" are relative terms that refer to the level of miRNAs found in a sample. In some embodiments, low and high miR expression is determined by comparison of miRNA levels in a group of control samples and test samples. Low and high expression can then be assigned to each sample based on whether the expression of mi in a sample is above (high) or below (low) the average or median miR expression level. For individual samples, high or low miR expression can be determined by comparison of the sample to a control or reference sample known to have high or low expression, or by comparison to a standard value. Low and high miR expression can include expression of either the precursor or mature forms of miRNA, or both.

Patient: As used herein, the term "patient" includes human and non-human animals. The preferred patient for treatment is a human. "Patient" and "subject" are used interchangeably herein.

Pharmaceutically acceptable vehicles: The pharmaceutically acceptable carriers (vehicles) useful in this disclosure are conventional. Remington's Pharmaceutical Sciences, by E. W. Martin, Mack Publishing Co., Easton, Pa., 15th Edition (1975), describes compositions and formulations suitable for pharmaceutical delivery of one or more therapeutic compounds, molecules or agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Screening: As used herein, "screening" refers to the process used to evaluate and identify candidate agents that affect such disease. Expression of a microRNA can be quantified using any one of a number of techniques known in the art and described herein, such as by microarray analysis or by qRT-PCR.

Small molecule: A molecule, typically with a molecular weight less than about 1000 Daltons, or in some embodiments, less than about 500 Daltons, wherein the molecule is capable of modulating, to some measurable extent, an activity of a target molecule.

Therapeutic: A generic term that includes both diagnosis and treatment.

Therapeutic agent: A chemical compound, small molecule, or other composition, such as an antisense compound, antibody, protease inhibitor, hormone, chemokine or cytokine, capable of inducing a desired therapeutic or prophylactic effect when properly administered to a subject.

As used herein, a "candidate agent" is a compound selected for screening to determine if it can function as a therapeutic agent. "Incubating" includes a sufficient amount of time for an agent to interact with a cell or tissue. "Contacting" includes incubating an agent in solid or in liquid form with a cell or tissue. "Treating" a cell or tissue with an agent includes contacting or incubating the agent with the cell or tissue.

Therapeutically-effective amount: A quantity of a specified pharmaceutical or therapeutic agent sufficient to achieve a desired effect in a subject, or in a cell, being treated with the agent. The effective amount of the agent will be dependent on several factors, including, but not limited to the subject or cells being treated, and the manner of administration of the therapeutic composition.

In some embodiments of the present methods, use of a control is desirable. In that regard, the control may be a non-cancerous tissue sample obtained from the same patient, or a tissue sample obtained from a healthy subject, such as a healthy tissue donor. In another example, the control is a standard calculated from historical values. Tumor samples and non-cancerous tissue samples can be obtained according to any method known in the art. For example, tumor and non-cancerous samples can be obtained from cancer patients that have undergone resection, or they can be obtained by extraction using a hypodermic needle, by microdissection, or by laser capture. Control (non-cancerous) samples can be obtained, for example, from a cadaveric donor or from a healthy donor.

In some embodiments, screening comprises contacting the candidate agents with cells. The cells can be primary cells obtained from a patient, or the cells can be immortalized or transformed cells.

The candidate agents can be any type of agent, such as a protein, peptide, small molecule, antibody or nucleic acid. In some embodiments, the candidate agent is a cytokine. In some embodiments, the candidate agent is a small molecule. Screening includes both high-throughout screening and screening individual or small groups of candidate agents.

MicroRNA Detection

In some methods herein, it is desirable to identify miRNAs present in a sample.

The sequences of precursor microRNAs (pre-miRNAs) and mature miRNAs are publicly available, such as through the miRBase database, available online by the Sanger Institute (see Griffiths-Jones et al., Nucleic Acids Res. 36:D154-D158, 2008; Griffiths-Jones et al., Nucleic Acids Res. 34:D140-D144, 2006; and Griffiths-Jones, Nucleic Acids Res. 32:D109-D111, 2004). The sequences of the precursor and mature forms of the presently disclosed preferred family members are provided herein.

Detection and quantification of RNA expression can be achieved by any one of a number of methods well known in the art (see, for example, U.S. Patent Application Publication Nos. 2006/0211000 and 2007/0299030, herein incorporated by reference) and described below. Using the known sequences for RNA family members, specific probes and primers can be designed for use in the detection methods described below as appropriate.

In some cases, the RNA detection method requires isolation of nucleic acid from a sample, such as a cell or tissue sample. Nucleic acids, including RNA and specifically miRNA, can be isolated using any suitable technique known in the art. For example, phenol-based extraction is a common method for isolation of RNA. Phenol-based reagents contain a combination of denaturants and RNase inhibitors for cell and tissue disruption and subsequent separation of RNA from contaminants. Phenol-based isolation procedures can recover RNA species in the 10-200-nucleotide range (e.g., precursor and mature miRNAs, 5S and 5.8S ribosomal RNA (rRNA), and U1 small nuclear RNA (snRNA)). In addition, extraction procedures such as those using TRIZOL™ or TRI REAGENT™, will purify all RNAs, large and small, and are efficient methods for isolating total RNA from biological samples that contain miRNAs and small interfering RNAs (siRNAs).

In some embodiments, use of a microarray is desirable. A microarray is a microscopic, ordered array of nucleic acids, proteins, small molecules, cells or other substances that enables parallel analysis of complex biochemical samples. A DNA microarray consists of different nucleic acid probes, known as capture probes that are chemically attached to a solid substrate, which can be a microchip, a glass slide or a microsphere-sized bead. Microarrays can be used, for example, to measure the expression levels of large numbers of messenger RNAs (mRNAs) and/or miRNAs simultaneously.

Microarrays can be fabricated using a variety of technologies, including printing with fine-pointed pins onto glass slides, photolithography using pre-made masks, photolithography using dynamic micromirror devices, ink-jet printing, or electrochemistry on microelectrode arrays.

Microarray analysis of miRNAs, for example (although these procedures can be used in modified form for any RNA analysis) can be accomplished according to any method known in the art (see, for example, PCT Publication No. WO 2008/054828; Ye et al., Nat. Med. 9(4):416-423, 2003; Calin et al., N. Engl. J. Med. 353(17):1793-1801, 2005, each of which is herein incorporated by reference). In one example, RNA is extracted from a cell or tissue sample, the small RNAs (18-26-nucleotide RNAs) are size-selected from total RNA using denaturing polyacrylamide gel electrophoresis. Oligonucleotide linkers are attached to the 5' and 3' ends of the small RNAs and the resulting ligation products are used as templates for an RT-PCR reaction with 10 cycles of amplification. The sense strand PCR primer has a fluorophore attached to its 5' end, thereby fluorescently labeling the sense strand of the PCR product. The PCR product is denatured and then hybridized to the microarray. A PCR product, referred to as the target nucleic acid that is complementary to the corresponding miRNA capture probe sequence on the array will hybridize, via base pairing, to the spot at which the capture probes are affixed. The spot will then fluoresce when excited using a microarray laser scanner. The fluorescence intensity of each spot is then evaluated in terms of the number of copies of a particular miRNA, using a number of positive and negative controls and array data normalization methods, which will result in assessment of the level of expression of a particular miRNA.

In an alternative method, total RNA containing the small RNA fraction (including the miRNA) extracted from a cell or tissue sample is used directly without size-selection of small RNAs, and 3' end labeled using T4 RNA ligase and either a fluorescently-labeled short RNA linker. The RNA samples are labeled by incubation at 30° C. for 2 hours followed by heat inactivation of the T4 RNA ligase at 80° C. for 5 minutes. The fluorophore-labeled miRNAs complementary to the corresponding miRNA capture probe sequences on the array will hybridize, via base pairing, to the spot at which the capture probes are affixed. The microarray scanning and data processing is carried out as described above.

There are several types of microarrays than be employed, including spotted oligonucleotide microarrays, pre-fabricated oligonucleotide microarrays and spotted long oligonucleotide arrays. In spotted oligonucleotide microarrays, the capture probes are oligonucleotides complementary to miRNA sequences. This type of array is typically hybridized with amplified PCR products of size-selected small RNAs from two samples to be compared (such as non-cancerous tissue and cancerous or sample tissue) that are labeled with two different fluorophores. Alternatively, total RNA containing the small RNA fraction (including the miRNAs) is extracted from the two samples and used directly without size-selection of small RNAs, and 3' end labeled using T4 RNA ligase and short RNA linkers labeled with two different fluorophores. The samples can be mixed and hybridized to one single microarray that is then scanned, allowing the visualization of up-regulated and down-regulated miRNA genes in one assay.

In pre-fabricated oligonucleotide microarrays or single-channel microarrays, the probes are designed to match the sequences of known or predicted miRNAs. There are commercially available designs that cover complete genomes (for example, from Affymetrix or Agilent). These microarrays give estimations of the absolute value of gene expression and therefore the comparison of two conditions requires the use of two separate microarrays.

Spotted long oligonucleotide arrays are composed of 50 to 70-mer oligonucleotide capture probes, and are produced by either ink-jet or robotic printing. Short Oligonucleotide Arrays are composed of 20-25-mer oligonucleotide probes, and are produced by photolithographic synthesis (Affymetrix) or by robotic printing.

In some embodiments, use of quantitative RT-PCR is desirable. Quantitative RT-PCR (qRT-PCR) is a modification of polymerase chain reaction used to rapidly measure the quantity of a product of polymerase chain reaction. qRT-PCR is commonly used for the purpose of determining whether a genetic sequence, such as a miR, is present in a sample, and if it is present, the number of copies in the sample. Any method of PCR that can determine the expression of a nucleic acid molecule, including a miRNA, falls within the scope of the present disclosure. There are several variations of the qRT-PCR method known in the art, three of which are described below.

Methods for quantitative polymerase chain reaction include, but are not limited to, via agarose gel electrophoresis, the use of SYBR Green (a double stranded DNA dye), and the use of a fluorescent reporter probe. The latter two can be analyzed in real-time.

With agarose gel electrophoresis, the unknown sample and a known sample are prepared with a known concentration of a similarly sized section of target DNA for amplification. Both reactions are run for the same length of time in identical conditions (preferably using the same primers, or at least primers of similar annealing temperatures). Agarose gel electrophoresis is used to separate the products of the reaction from their original DNA and spare primers. The relative quantities of the known and unknown samples are measured to determine the quantity of the unknown.

The use of SYBR Green dye is more accurate than the agarose gel method, and can give results in real time. A DNA binding dye binds all newly synthesized double stranded DNA and an increase in fluorescence intensity is measured, thus allowing initial concentrations to be determined. However, SYBR Green will label all double-stranded DNA, including any unexpected PCR products as well as primer dimers, leading to potential complications and artifacts. The reaction is prepared as usual, with the addition of fluorescent double-stranded DNA dye. The reaction is run, and the levels of fluorescence are monitored (the dye only fluoresces when bound to the double-stranded DNA). With reference to a standard sample or a standard curve, the double-stranded DNA concentration in the PCR can be determined.

The fluorescent reporter probe method uses a sequence-specific nucleic acid based probe so as to only quantify the probe sequence and not all double stranded DNA. It is commonly carried out with DNA based probes with a fluorescent reporter and a quencher held in adjacent positions (so-called dual-labeled probes). The close proximity of the reporter to the quencher prevents its fluorescence; it is only on the breakdown of the probe that the fluorescence is detected. This process depends on the 5' to 3' exonuclease activity of the polymerase involved.

The real-time quantitative PCR reaction is prepared with the addition of the dual-labeled probe. On denaturation of the double-stranded DNA template, the probe is able to bind to its complementary sequence in the region of interest of the template DNA. When the PCR reaction mixture is heated to activate the polymerase, the polymerase starts synthesizing the complementary strand to the primed single stranded template DNA. As the polymerization continues, it reaches the probe bound to its complementary sequence, which is then hydrolyzed due to the 5'-3' exonuclease activity of the polymerase, thereby separating the fluorescent reporter and the quencher molecules. This results in an increase in fluorescence, which is detected. During thermal cycling of the real-time PCR reaction, the increase in fluorescence, as released from the hydrolyzed dual-labeled probe in each PCR cycle is monitored, which allows accurate determination of the final, and so initial, quantities of DNA.

In some embodiments, use of in situ hybridization is desirable. In situ hybridization (ISH) applies and extrapolates the technology of nucleic acid hybridization to the single cell level, and, in combination with the art of cytochemistry, immunocytochemistry and immunohistochemistry, permits the maintenance of morphology and the identification of cellular markers to be maintained and identified, and allows the localization of sequences to specific cells within populations, such as tissues and blood samples. ISH is a type of hybridization that uses a complementary nucleic acid to localize one or more specific nucleic acid sequences in a portion or section of tissue (in situ), or, if the tissue is small enough, in the entire tissue (whole mount ISH). RNA ISH can be used to assay expression patterns in a tissue, such as the expression of miRNAs.

Sample cells or tissues are treated to increase their permeability to allow a probe, such as a miRNA-specific probe, to enter the cells. The probe is added to the treated cells, allowed to hybridize at pertinent temperature, and excess probe is washed away. A complementary probe is labeled with a radioactive, fluorescent or antigenic tag, so that the probe's location and quantity in the tissue can be determined using autoradiography, fluorescence microscopy or immunoassay. The sample may be any sample as herein described, such as a non-cancerous or cancerous tissue sample. Since the sequences of miR-155 family members are known, miR-155 probes can be designed accordingly such that the probes specifically bind miR-155.

In some embodiments, use of in situ PCR is desirable. In situ PCR is the PCR based amplification of the target nucleic acid sequences prior to ISH. For detection of RNA, an intracellular reverse transcription step is introduced to generate complementary DNA from RNA templates prior to in situ PCR. This enables detection of low copy RNA sequences.

Prior to in situ PCR, cells or tissue samples are fixed and permeabilized to preserve morphology and permit access of the PCR reagents to the intracellular sequences to be amplified. PCR amplification of target sequences is next performed either in intact cells held in suspension or directly in cytocentrifuge preparations or tissue sections on glass slides. In the former approach, fixed cells suspended in the PCR reaction mixture are thermally cycled using conventional thermal cyclers. After PCR, the cells are cytocentrifuged onto glass slides with visualization of intracellular PCR products by ISH or immunohistochemistry. In situ PCR on glass slides is performed by overlaying the samples with the PCR mixture under a coverslip which is then sealed to prevent evaporation of the reaction mixture. Thermal cycling is achieved by placing the glass slides either directly on top of the heating block of a conventional or specially designed thermal cycler or by using thermal cycling ovens.

Detection of intracellular PCR products is generally achieved by one of two different techniques, indirect in situ PCR by ISH with PCR-product specific probes, or direct in situ PCR without ISH through direct detection of labeled nucleotides (such as digoxigenin-11-dUTP, fluorescein-dUTP, 3H-CTP or biotin-16-dUTP), which have been incorporated into the PCR products during thermal cycling.

Use of differentially-expressed miR5 and miRNAs as predictive markers of prognosis and for identification of therapeutic agents. It is disclosed herein that certain expression patterns of miR-155, along with status indicators are predictors of survival prognosis in certain patients. As used herein, "poor prognosis" generally refers to a decrease in survival, or in other words, an increase in risk of death or a decrease in the time until death. Poor prognosis can also refer to an increase in severity of the disease, such as an increase in spread (metastasis) of the cancer to other organs. In one embodiment, the respective markers show at least a 1.5-fold increase or decrease in expression relative to the control. In other embodiments, poor prognosis is indicated by at least a 2-fold, at least a 2.5-fold, at least a 3-fold, at least a 3.5-fold, or at least a 4-fold increase or decrease in the markers relative to the wild-type tumor control figures.

Methods of screening candidate agents to identify therapeutic agents for the treatment of disease are well known in the art. Methods of detecting expression levels of RNA and proteins are known in the art and are described herein, such as, but not limited to, microarray analysis, RT-PCR (including qRT-PCR), in situ hybridization, in situ PCR, and Northern blot analysis. In one embodiment, screening comprises a high-throughput screen. In another embodiment, candidate agents are screened individually.

The candidate agents can be any type of molecule, such as, but not limited to nucleic acid molecules, proteins, peptides, antibodies, lipids, small molecules, chemicals, cytokines, chemokines, hormones, or any other type of molecule that may alter cancer disease state(s) either directly or indirectly.

Typically, an endogenous gene, miRNA or mRNA is modulated in the cell. In particular embodiments, the nucleic acid sequence comprises at least one segment that is at least 70, 75, 80, 85, 90, 95, or 100% identical in nucleic acid sequence to one or more miRNA sequence listed in Table 1. Modulation of the expression or processing of an endogenous gene, miRNA, or mRNA can be through modulation of the processing of an mRNA, such processing including transcription, transportation and/or translation with in a cell. Modulation may also be effected by the inhibition or enhancement of miRNA activity with a cell, tissue, or organ. Such processing may effect the expression of an encoded product or the stability of the mRNA. In still other embodiments, a nucleic acid sequence can comprise a modified nucleic acid sequence. In certain aspects, one or more miRNA sequence may include or comprise a modified nucleobase or nucleic acid sequence.

It will be understood in methods of the invention that a cell or other biological matter such as an organism (including patients) can be provided an miRNA or miRNA molecule corresponding to a particular miRNA by administering to the cell or organism a nucleic acid molecule that functions as the corresponding miRNA once inside the cell. The form of the molecule provided to the cell may not be the form that acts a miRNA once inside the cell. Thus, it is contemplated that in some embodiments, biological matter is provided a synthetic miRNA or a nonsynthetic miRNA, such as one that becomes processed into a mature and active miRNA once it has access to the cell's miRNA processing machinery. In certain embodiments, it is specifically contemplated that the miRNA molecule provided to the biological matter is not a mature miRNA molecule but a nucleic acid molecule that can be processed into the mature miRNA once it is accessible to miRNA processing machinery. The term "nonsynthetic" in the context of miRNA means that the miRNA is not "synthetic," as defined herein. Furthermore, it is contemplated that in embodiments of the invention that concern the use of synthetic miRNAs, the use of corresponding nonsynthetic miRNAs is also considered an aspect of the invention, and vice versa. It will be understand that the term "providing" an agent is used to include "administering" the agent to a patient.

In certain embodiments, methods also include targeting a miRNA to modulate in a cell or organism. The term "targeting a miRNA to modulate" means a nucleic acid of the invention will be employed so as to modulate the selected miRNA. In some embodiments the modulation is achieved with a synthetic or non-synthetic miRNA that corresponds to the targeted miRNA, which effectively provides the targeted miRNA to the cell or organism (positive modulation). In other embodiments, the modulation is achieved with a miRNA inhibitor, which effectively inhibits the targeted miRNA in the cell or organism (negative modulation).

In some embodiments, the miRNA targeted to be modulated is a miRNA that affects a disease, condition, or pathway. In certain embodiments, the miRNA is targeted because a treatment can be provided by negative modulation of the targeted miRNA. In other embodiments, the miRNA is targeted because a treatment can be provided by positive modulation of the targeted miRNA.

In certain methods of the invention, there is a further step of administering the selected miRNA modulator to a cell, tissue, organ, or organism (collectively "biological matter") in need of treatment related to modulation of the targeted miRNA or in need of the physiological or biological results discussed herein (such as with respect to a particular cellular pathway or result like decrease in cell viability). Consequently, in some methods of the invention there is a step of identifying a patient in need of treatment that can be provided by the miRNA modulator(s). It is contemplated that an effective amount of a miRNA modulator can be administered in some embodiments. In particular embodiments, there is a therapeutic benefit conferred on the biological matter, where a "therapeutic benefit" refers to an improvement in the one or more conditions or symptoms associated with a disease or condition or an improvement in the prognosis, duration, or status with respect to the disease. It is contemplated that a therapeutic benefit includes, but is not limited to, a decrease in pain, a decrease in morbidity, a decrease in a symptom. For example, with respect to cancer, it is contemplated that a therapeutic benefit can be inhibition of tumor growth, prevention of metastasis, reduction in number of metastases, inhibition of cancer cell proliferation, inhibition of cancer cell proliferation, induction of cell death in cancer cells, inhibition of angiogenesis near cancer cells, induction of apoptosis of cancer cells, reduction in pain, reduction in risk of recurrence, induction of chemo- or radiosensitivity in cancer cells, prolongation of life, and/or delay of death directly or indirectly related to cancer.

Furthermore, it is contemplated that the miRNA compositions may be provided as part of a therapy to a patient, in conjunction with traditional therapies or preventative agents. Moreover, it is contemplated that any method discussed in the context of therapy may be applied as preventatively, particularly in a patient identified to be potentially in need of the therapy or at risk of the condition or disease for which a therapy is needed.

In addition, methods of the invention concern employing one or more nucleic acids corresponding to a miRNA and a therapeutic drug. The nucleic acid can enhance the effect or efficacy of the drug, reduce any side effects or toxicity, modify its bioavailability, and/or decrease the dosage or frequency needed. In certain embodiments, the therapeutic drug is a cancer therapeutic. Consequently, in some embodiments, there is a method of treating cancer in a patient comprising administering to the patient the cancer therapeutic and an effective amount of at least one miRNA molecule that improves the efficacy of the cancer therapeutic or protects non-cancer cells. Cancer therapies also include a variety of combination therapies with both chemical and radiation based treatments. Combination chemotherapies include but are not limited to, for example, bevacizumab, cisplatin (CDDP), carboplatin, EGFR inhibitors (gefitinib and cetuximab), procarbazine, mechlorethamine, cyclophosphamide, camptothecin, COX-2 inhibitors (e.g., celecoxib) ifosfamide, melphalan, chlorambucil, busulfan, nitrosurea, dactinomycin, daunorubicin, doxorubicin (adriamycin), bleomycin, plicomycin, mitomycin, etoposide (VP16), tamoxifen, raloxifene, estrogen receptor binding agents, taxol, taxotere, gemcitabien, navelbine, farnesyl-protein transferase inhibitors, transplatinum, 5-fluortheouracil, vincristin, vinblastin and methotrexate, or any analog or derivative variant of the foregoing.

Generally, inhibitors of miRNAs can be given to achieve the opposite effect as compared to when nucleic acid molecules corresponding to the mature miRNA are given. Similarly, nucleic acid molecules corresponding to the mature miRNA can be given to achieve the opposite effect as compared to when inhibitors of the miRNA are given. For example, miRNA molecules that increase cell proliferation can be provided to cells to increase proliferation or inhibitors of such molecules can be provided to cells to decrease cell proliferation. The present invention contemplates these embodiments in the context of the different physiological effects observed with the different miRNA molecules and miRNA inhibitors disclosed herein. These include, but are not limited to, the following physiological effects: increase and decreasing cell proliferation, increasing or decreasing apoptosis, increasing transformation, increasing or decreasing cell viability, reduce or increase viable cell number, and increase or decrease number of cells at a particular phase of the cell cycle. Methods of the invention are generally contemplated to include providing or introducing one or more different nucleic acid molecules corresponding to one or more different miRNA molecules. It is contemplated that the following, at least the following, or at most the following number of different nucleic acid molecules may be provided or introduced: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or any range derivable therein. This also applies to the number of different miRNA molecules that can be provided or introduced into a cell.

miRNA-155

The mutator phenotype that results from MMR dysfunction induces the acquisition of additional gene mutations that promote cancer progression. In addition to germline mutations, there are a number of pathogenic events that result in the reduced or absent expression of core MMR proteins including promoter methylation and reduced histone acetylation as well as micro environmental factors such as inflammation and hypoxia. The inventors' results provide that miR-155 plays a role in this multi-factorial regulation by causing down-modulation of the core MMR heterodimeric proteins MSH2-MSH6 and MLH1-PMS2. The simultaneous inhibition of these essential MMR components by miR-155 causes a mutator phenotype.

Without being bound by any particular theory, the remarkable effect that miR-155 exerts on the entire MMR system is likely a result of two different phenomena. First, MMR protein stability is linked to their ability to form heterodimers; therefore, loss of the hMSH2 and hMLH1 proteins results in destabilization of their respective heterodimeric complex proteins. Second, miR-155 appears to target the down-regulation of core MMR proteins. Together, these regulatory and stability alterations result in a significant increase in mutation rates. The inventors cannot eliminate the possibility that miR155 affects other related DNA repair proteins, enhancing the phenotypic effect of MMR defects by unrelated genomic processes.

Incomplete repression MMR proteins by miR-155 are not unique for tumor suppressor genes in cancer. A partial (50%) reduction in the expression of one allele of the Adenomatous Polyposis Coli (APC) gene has been correlated with the development of colorectal cancer. Moreover, the reduced expression of a single allele of the Transforming Growth Factor β Receptor I (TGFBR1) gene has been linked to CRC. MicroRNAs have recently been proposed as trans-activating elements involved in allelic and gene expression regulation. The inventors' results strongly support a role for miRNAs in the non-mendelian regulation of MMR genes.

The complexity of miRNA regulation is increased by the tissue-specificity and by possible polymorphisms in the target sequences. For example, acquired mutations in the 3'UTR of hMLH1 have been linked to disease relapse in patients with acute myeloid leukemia. The inventors can not exclude the possibility that over-expression of miR-155 combined with acquired mutations in the 3'UTR of MMR target genes further contributes to the development of MSI in these selected patients. Moreover, well-defined mutations and/or epigenetic inactivation of MMR genes appear less frequent in specific subsets of MSI tumors, such as CRC associated with Inflammatory Bowel Diseases and Non-Hodgkin lymphomas associated with HIV infection. The inventors' studies demonstrating down-regulation of core MMR genes suggest that a potential alternative pathogenetic mechanism for these cancers may be overexpression of miR-155.

Although the inventors observed an inverse correlation between miR-155 and the expression of MMR proteins in CRC, not all the tumors with increased miR-155 expression are characterized by MSI. In human cells several factors might account for the differing regulation of the core MMR proteins by miR-155 including a threshold expression effect or savage loops involved in the fine tuning of miRNA and gene expression.

Patients with MMR deficient tumors are largely characterized by good prognosis but a lower survival advantage after 5-Fluorouracil adjuvant chemotherapy when compared with patients with MMR proficient tumors. The contributing role of miR-155 in the downregulation of the core MMR proteins suggests that miR-155 might be an important stratification factor in the prognosis and therapeutics of cancer patients. miR-155 expression may be an additional analytical test in etiology of MSI tumors where the standard tests do not provide a conclusive diagnosis.

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

EXAMPLES

Example 1

Materials and Methods Used

Cell Cultures and Transfection

Colo-320 DM, HCT-116 and DLD-1 colorectal cancer (CRC) cells (American Type Culture Collection ATCC Manassas, Va.) were cultured in RPMI 1640 (Gibco, Carlsbad, Calif.), MV4-11 B myelomonocytic leukemia cells (ATCC Manassas, Va.) and packaging cells 293TN (System Biosciences, Mountain View, Calif.) were grown in DMEM (Gibco, Carlsbad, Calif.). All cells were supplemented with 10% fetal bovine serum (Sigma, St. Louis, Mo.) plus antibiotics. Cells were checked for Mycoplasma contamination periodically and before functional experiments and were always found negative. Cells were transfected in 6-well plates by using Lipofectamine 2000 (Invitrogen, Carlsbad, Calif.) following manufacturer's protocol. For over-expression studies specific miRNA or control precursor oligonucleotides were purchased from Ambion (Austin, Tex.) and used at 100 nM. For silencing experiments miRCURY LNA™ anti-miR-155 or control miRCURY knockdown probe (Exiqon, Vedbaek, Denmark) were used at 100 nM. miRNA expression was verified after 48 hours by quantitative real time PCR as described below. Plasmids encoding the full length MLH1 and MSH6 cDNA were purchased from Origene. The MLH1 and MSH6 mutants for the miR-155 seed regions were prepared using QuikChange site-directed mutagenesis kit (Stratagene, San Diego, Calif.). $0.3 \times 10^6$ cells were seeded in a 6 well plate and transfected after 24 using 1 ug of WT or mutant cDNA encoding plasmid and 1 ug of miR-155 encoding vector or empty vector cells were harvested after 36 h and lysates analyzed by Western Blotting Luciferase Assay The predicted miRNA binding sites in the 3'-UTR and/or CDS of hMLH1, hMSH2 and hMSH6 were cloned downstream of the firefly luciferase gene as follows. Complimentary (cDNA) from SW-480 cells was amplified by PCR using specific primers (Table 2 below).

The product was then digested with SpeI and SacII (New England Biolabs Ipswich, Mass.) and inserted into the pGL3 control vector (Promega, Madison, Wis.) previously modified to harbor the SpeI and SacII sites immediately downstream of the stop codon of the firefly luciferase gene. Reporter constructs with mutated miRNA recognition sequences were constructed for each single gene (MUT-155). For hMSH2 3'UTR and hMLH1 3'UTR binding sites the sequence complementary to the seed of miR-155 was deleted using a QuikChange site-directed mutagenesis kit. For all the other miR-155 seed regions mutant constructs were obtained using primers sited up or downstream of the predicted miRNA binding site in order to exclude the seed-region complementary sites. Primer sequences are presented in Table 2.

Colo-320 DM cells were co-transfected in 12-well plates with 1 μg of pGL3 firefly luciferase reporter control vector, 0.1 μg of the phRL-SV40 control vector (Promega, Madison, Wis.), and 100 nM miRNA or control precursors. Firefly and Renilla luciferase activities were measured consecutively by using the Dual Luciferase Assay (Promega) 24 hours after transfection.

Western Blotting

For immunoblotting analysis cells were lysed with ice-cold Cell Lysis Buffer plus protease inhibitor (Cell Signaling Technology Inc. Danvers, Mass.). Equivalent amounts of protein were resolved and mixed with 4×SDS-PAGE sample buffer, electrophoresed in a 4%-20% and 7.5% linear gradient Tris-HCL Criterion Precast Gels (Bio-Rad), and transferred to nitrocellulose or PVDF membranes (Bio-Rad). The membranes were blocked with 5% nonfat dry milk in Tris-buffered saline, pH 7.4, containing 0.05% Tween 20, and were incubated with primary and secondary antibodies according to the manufacturer's instructions. The following primary antibodies were used: mouse monoclonal anti-MSH2 (1:200, Invitrogen), mouse monoclonal anti-MSH6 (1:500, BD Biosciences San Jose, Calif.), mouse monoclonal anti-MLH1 (1:200, Invitrogen), rabbit polyclonal anti-MLH1 (1:200 used for mouse experiments SantaCruz Biotechnology, Santa Cruz, Calif.), mouse monoclonal anti-actin (1:5000, Sigma), mouse monoclonal anti-GAPDH (1:1000, SantaCruz Biotechnology). N-terminal primary antibodies against MLH1 and MSH6 (1/500 Sigma).

Real Time PCR for Mature miRNAs and Genes

Total RNA was isolated with Trizol (Invitrogen). Mature miRNAs were assessed by the singletube TaqMan MicroRNA Assay, while the expression of mRNAs of interest evaluated by the Gene Expression Assay with the following probes: hMLH1=Hs00979923_m1, hMSH2=Hs00953523_m1, hMSH6=Hs00943001_m1 (Applied Biosystems, Foster City, Calif.). miRNA expression was normalized to that of RNU44 and RNU48 in humans and to snoR-135 in mouse cells. Gene expression was normalized to vinculin. All retrotranscriptase (RT) reactions, including no-template controls and RT minus controls, were run in a GeneAmp PCR 9700 Thermocycler (Applied Biosystems). Each sample was tested in triplicate unless otherwise specified.

Northern Blotting

For mature miRNA detection, acrilamide Northern blotting was performed as previously described.

Generation of Stable Clones Over-Expressing miR-155

Colo-320 DM cells were stably infected with the pCDH-CMV-MCS-EF1-miRNA expression plasmid containing the full-length miR-155 and the GFP gene under the control of two different promoters (System Biosciences, Mountain View, Calif.). An empty vector was used as control. Pre-miR-155 expression and control constructs were packaged with pPACKH1 Lentivector Packaging Plasmid mix (System Biosciences) in 293-TN packaging cell line. Viruses were concentrated using PEG-It™ Virus Precipitation Solution and titers analyzed using UltraRapid Lentiviral Titer Kit (System Biosciences). Infected cells were selected by FACS analysis (FACS Calibur, Becton Dickinson Immunocytometry Systems). Infection efficiency 90% was verified by fluorescent microscopy and further confirmed by real time PCR for miR-155 expression.

Histopathologic Evaluation

Tumor type (adenocarcinoma and mucinous adenocarcinoma) and grade of differentiation were determined according to WHO criteria. Carcinomas with a predominant solid growth pattern and mild or moderate nuclear pleomorphism were classified as medullary adenocarcinomas.

Immunohistochemical Analysis

Immunohistochemical analysis of MLH1 and PMS2 expression was performed according to the analytic procedure described previously. Tumors showing complete loss of nuclear MLH1 or MSH2 expression were classified as MLH1negative or MSH2negative. Nuclear immunostaining of normal epithelial cells, lymphocytes, and stromal cells served as internal positive controls in each case. All tumors were evaluated independently by two pathologists without knowledge of clinical data and MSI status.

Tissue Collection

Fresh frozen tissues from tumor and normal adjacent tissue from 83 consecutive cases of CRC were collected at the Istituto Scientifico Romagnolo per lo Studio e la Cura dei Tumori, Meldola, Italy after approval of the ethical committee. Cell lysates for protein and RNA extraction were extracted as above mentioned.

Laser Captere Microdissection (LCM)

LCM was performed the OSU Laser Capture Microdissection and Image Analysis Core Facility.

MLH1 and PMS2 Sequencing

DNA from CRC patients was amplified and sequenced. A 3730 DNA Analyzer and the ABI Prism BigDye Terminator Cycle Sequencing Kit version 3.1 were used for the sequencing analysis. Data collection software v3.0 and sequencing analysis software v5.2 were used. Patient information and tissues have been collected after approval of the institutional ethical committee.

Example 2

Transfections

Colo-320 DM, HCT-116, and DLD1 cells were transfected by using Lipofectamine 2000 (Invitrogen, Carlsbad, Calif.), while MV4-11 Lentiviral vectors for miR-155 over-expression and empty vector were generated by System Biosciences (Mountain View, Calif.) according to the manufacturer's instructions. Microsatellite instability was evaluated by genotyping analysis using diagnostic primers. Genomic DNA from MSI patients was sequenced. Statistical analysis: results are expressed as mean±standard error (S.E.M), unless indicated otherwise. Comparisons between groups were performed using the two-tailed Student's t test. Significance was accepted when p was less than 0.05. Graphpad Prism v5.0 (Graphpad Software Inc.) analysis was used for the Pearson's correlation.

Example 3 hMLH1, hMSH2 and hMSH6 are Targets of miR-155

The inventors used in silico prediction models to identify potential binding sites for miR-155 in the mRNA of the core MMR genes. Two putative sites were found in hMLH1 using RNAhybrid (BiBiServ, Germany; NCBI NM_000249.2), one in the 3'-UTR and the other in the coding sequence (CDS) of (NCBI NM_000249.2); one site in the 3'-UTR of hMSH2 using TargetScan (Whitehead Institute, MIT; NCBI NM_000251.1); and one in the CDS of hMSH6 using RNAhybrid (BiBiServ, Germany; NCBI NM_000179.2) (FIG. 1A; FIG. 6).

As a functional screen the inventors subcloned the coding and 3'-regions including the predicted miR-155 seed regions of MLH1, MSH2 or MSH6 downstream of the luciferase gene and recorded Luciferase protein activity. The inventors used MMR proficient colo-320 DM CRC cells for these studies since they contain a low basal level of miR-155. The Colo-320 DM cells were transfected with the luciferase reporter constructs and with a miR-155 precursor (pre-miR-155) or control precursor (pre-miR control).

Figure 1B:
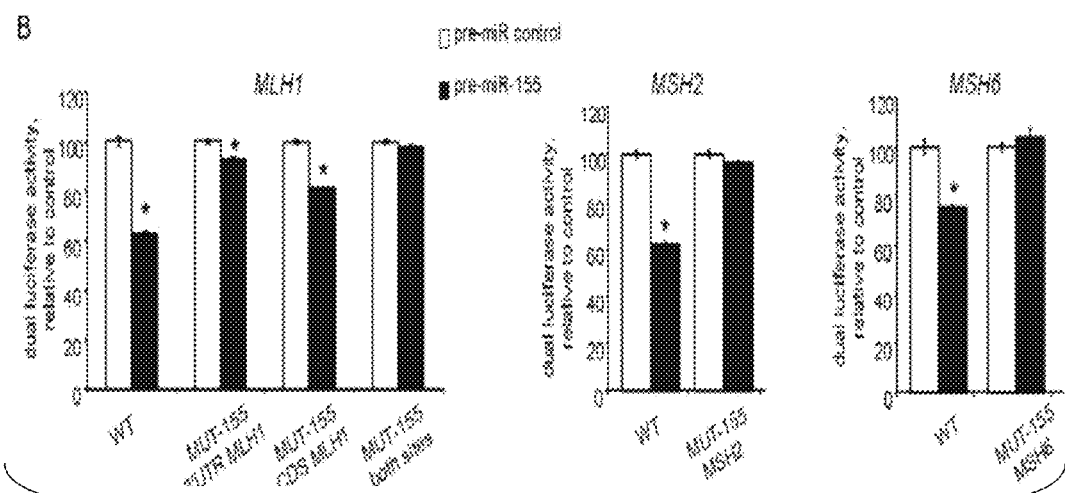

The inventors observed a reduction of 37%, 38% and 24% in the luciferase activity in the presence of pre-miR-155 with constructs containing the miR-155 seed regions of MLH1, MSH2 or MSH6, respectively ($p<0.001$; FIG. 1Bb; see WT for each). No changes were observed in the luciferase activity when the constructs contained a deletion of the miR155 seed region (FIG. 1B; see MUT-155 for each construct). Interestingly, the effect of the individual miR-155 binding sites in the hMLH1 gene appeared additive (FIG. 1B; compare hMLH1 MUT-155 3'-UTR and MUT-155 CDS to WT).

Ribosomes Displace the miRNA-RISC Complex from a CDS Target Site.

This process results in the inability of microRNAs to modulate a target protein. Both MLH1 and MSH6 contain CDS seed regions (FIG. 1; FIG. 6).

Figure 7:
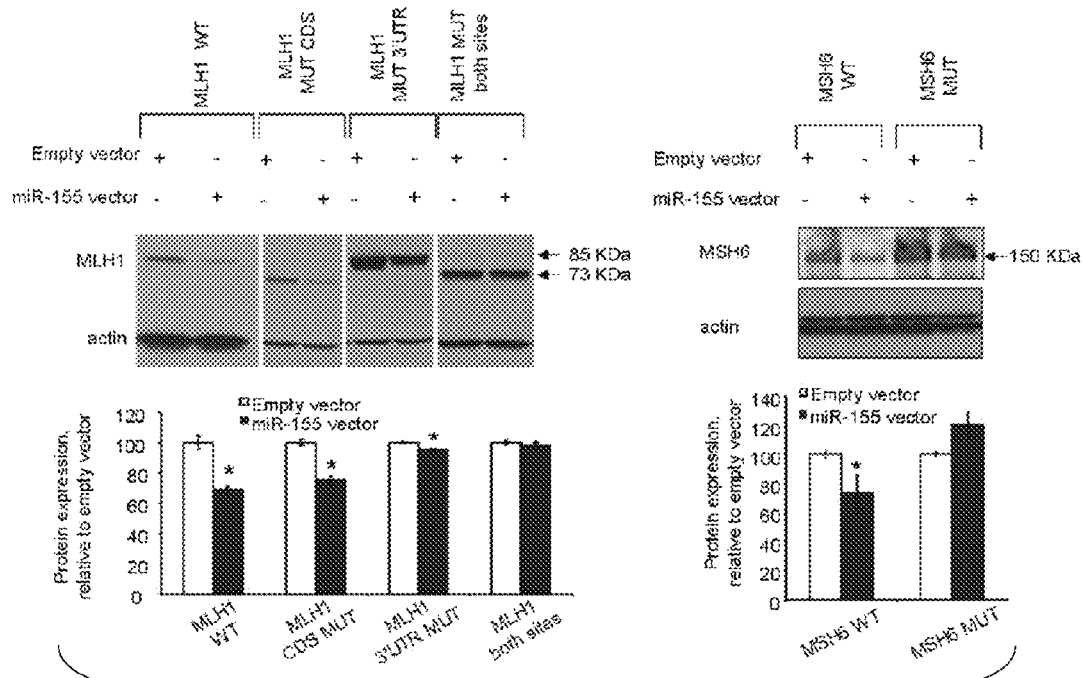
FIG. 7: miR-155 and MMR proteins expression in CRC tissues. MiR-155 regulates exogenous expression of MLH1 and MSH6. HCT-116 and DLD-1 cell lines lacking MLH1 and MSH6 respectively were co-transfected with plasmid encoding MLH1 or MSH6 proteins and miR-155 expressing vector or scrambled vector. Co-transfection with miR-155 induced a reduction in MLH1 and MSH6 protein expression. Disruption of the binding sites in the CDS of MLH1 and MSH6 resulted in the expression of a truncated protein (73 KD and 150 KD respectively). An N-terminal antibody against MLH1 and MSH6 was used to detect both the WT and the truncated proteins. The shift in protein size is less detectable in case of MSH6 due to the higher molecular weight and the use of a 4-20 gradient gel. Even in presence of a truncated protein MLH1 deregulation was still present due to the conserved 3'UTR binding site. Disruption of both MLH1 seed regions resulted in loss of activity of miR-155. Representative blots along with normalization of 3 different experiments are shown. Bars represent mean and S.E.M. * p<0.005 relative to empty vector.
Figure 8A:
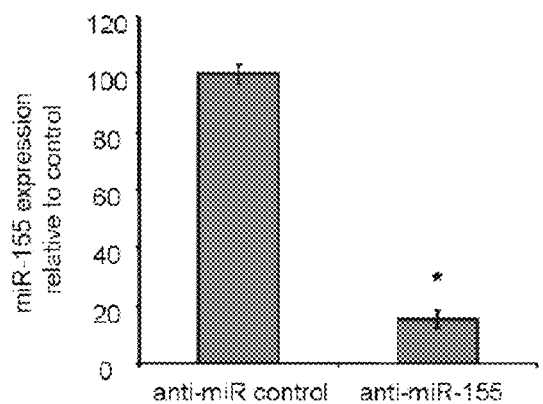
Figure 8B:
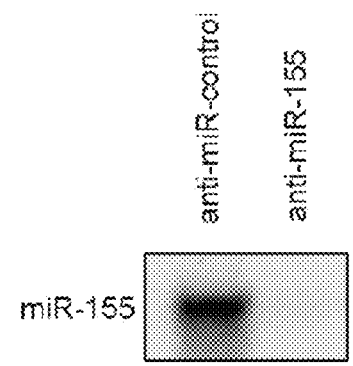

To examine the possibility of miRNA-RISC displacement, the inventors co-transfected cell lines lacking MLH1 (HCT116) or MSH6 (DLD1) with a mammalian expression vector containing the corresponding full-length cDNA with or without the miR-155 precursor, and examined protein expression (FIG. 7).

The inventors deleted the CDS miR-155 target site in the hMLH1 and hMSH6 cDNA sequence to determine whether expression might be affected by miRNA-RISC ribosome displacement. In-frame deletion of the CDS miR-155 seed sequence resulted in a truncated hMLH1 and hMSH6 protein (FIG. 7; size reduction of the 160 kD hMSH6 is only detectable in longer gel runs). Co-transfection of the MMR cDNAs with the miR-155 expression vector resulted in down-regulation of hMLH1 and hMSH6 proteins (FIG. 7; see hMLH1 WT and hMSH6 WT). Deletion of the CDS miR-155 seed sequence from the cDNA resulted in partial recovery of hMLH1 expression (FIG. 7; see hMLH1 MUT CDS) and complete recovery of hMSH6 expression (FIG. 7; see hMSH6 MUT). Mutation of both the hMLH1 CDS and 3'-UTR seed sequences resulted in a complete recovery of hMLH1 protein expression (FIG. 7; see hMLH1 double mutant). These results are qualitatively similar to the Luciferase-based system containing the miR-155 seed sequence from hMLH1 and hMSH6 (FIG. 1B), and show that miRNA-RISC ribosome displacement is unlikely to be an issue in miR-155 modulation of MMR proteins.

Figure 2A:
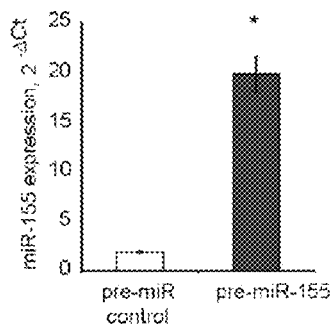
FIGS. 2A-2C: Over-expression of miR-155 decreases the expression of MLH1, MSH2 and MSH6 in CRC cells. Colo-320 DM cells were transfected with pre-miR-155, pre-miR control or siRNA against selected genes for 48 hours.

The effect of miR-155 on endogenous MMR gene and protein expression was examined in colo-320 DM cells (FIG. 2). A consistent increase in pre-miR-155 compared to a scrambled pre-miR control was determined by quantitative PCR (qPCR) for the transfected colo-320 DM cells (FIG. 2A).

Figure 2B:
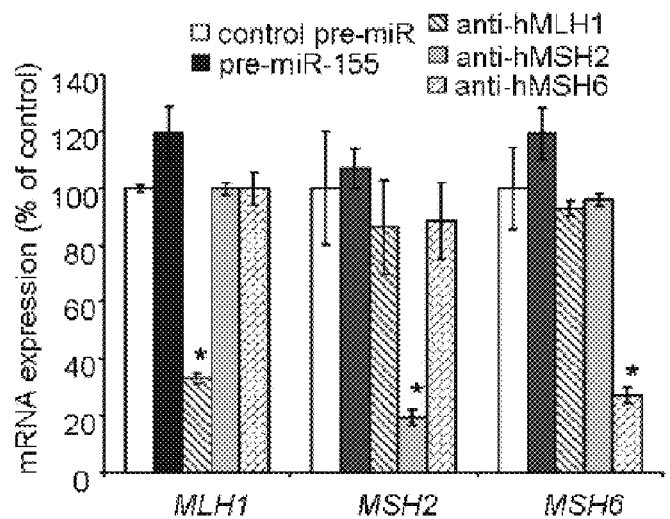

The inventors found that the mRNA expression of hMLH1, hMSH2 and hMSH6 was unaffected by pre-miR-155 overexpression (FIG. 2B, compare white and blue bars). In contrast, the hMLH1, hMSH2 and hMSH6 proteins were reduced by $53\pm14\%$ ($p=0.02$), $37\pm10\%$ ($p=0.01$) and $32\pm7.4\%$ ($p=0.004$) in cells transfected with pre-miR-155, respectively (FIG. 2C; left panel, compare white and blue bars right panel).

Figure 2C:
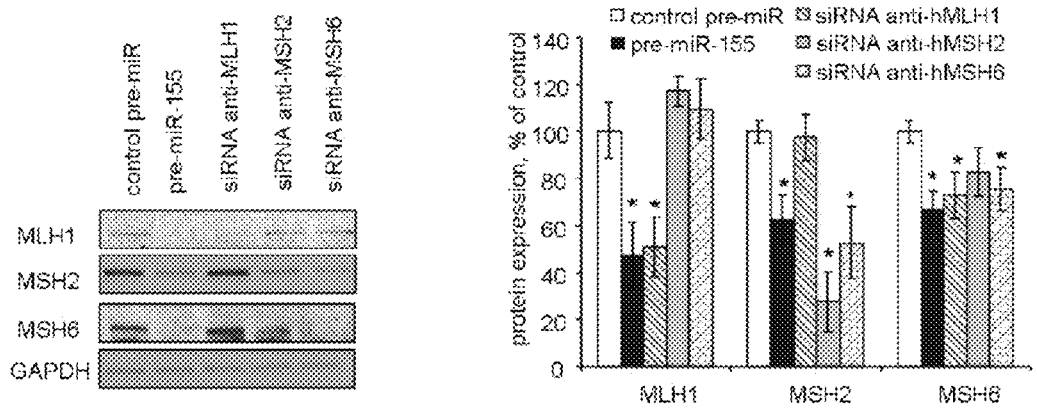

To assure the inventors were capable of detecting changes in mRNA expression, the inventors performed siRNA knock down studies in the colo-320 DM cells (FIG. 2B and FIG. 2C). The inventors found siRNA MMR gene-specific reduction of mRNA expression as would be expected (FIG. 2B; left hatched, light blue, right hatched bars). The reduction in mRNA translated to a reduction in corresponding MMR proteins (FIG. 2C; left hatched, light blue, right hatched bars). Moreover, the inventors found that the stability of the hMSH6 protein was linked to the expression of hMSH2 protein. These results show that miR-155 exerts its greatest affect on MMR proteins by post-translational inhibition.

To confirm the modulation of MMR proteins by miR-155 the inventors examined MV4-11 cells that over-express miR-155 (FIGS. 8A-8D). In these studies MV4-11 cells were transfected with a sequence-specific locked nucleic acid (LNA) modified oligonucleotide that targets miR-155 knock down (anti-miR-155; Ambion) as well as a control LNA anti-miRNA. A 6.7-fold reduction in miR-155 was observed by qPCR (FIG. 8A) that was confirmed by Northern blot analysis (FIG. 8B) when the LNA anti-miR-155 oligonucleotide was transfected compared to the nonspecific LNA anti-miR control.

The inventors also observed an increase in hMLH1, hMSH2, and hMSH6 proteins in MV4-11 cells transfected with LNA anti-miR-155 FIG. 8C) compared to the LNA anti-miR control transfections by Western analysis (FIG. 8D). Together with the colo-320 DM miR-155 over-expression data, these results suggest that the levels of cellular miR-155 have a direct effect on the expression of the core MMR proteins.

Example 4

Over-Expression of miR-155 Induces a Mutator Phenotype

Figures 3A, 3B:
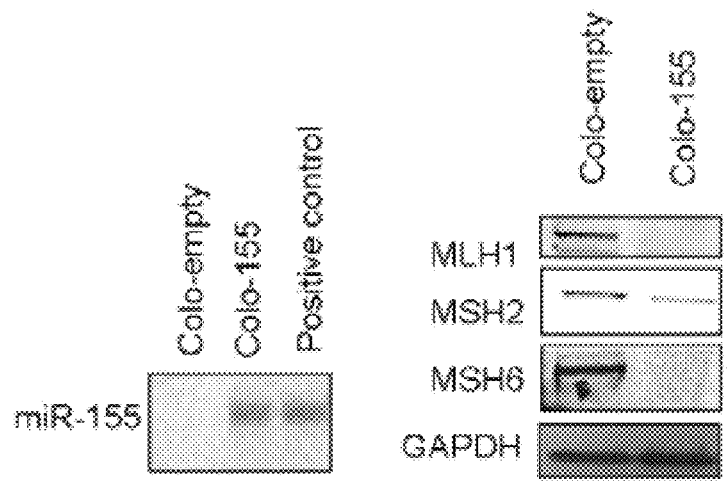
FIGS. 3A-3D: Stable clones with over-expression of miR-155. The functional effect of miR-155 over-expression on colon cancer cell lines. MMR proficient Colo-320 DM cells were stably infected with a lentiviral vector over-expressing miR-155 (Colo-155) or an empty vector (Coloempty).
Figure 3C:
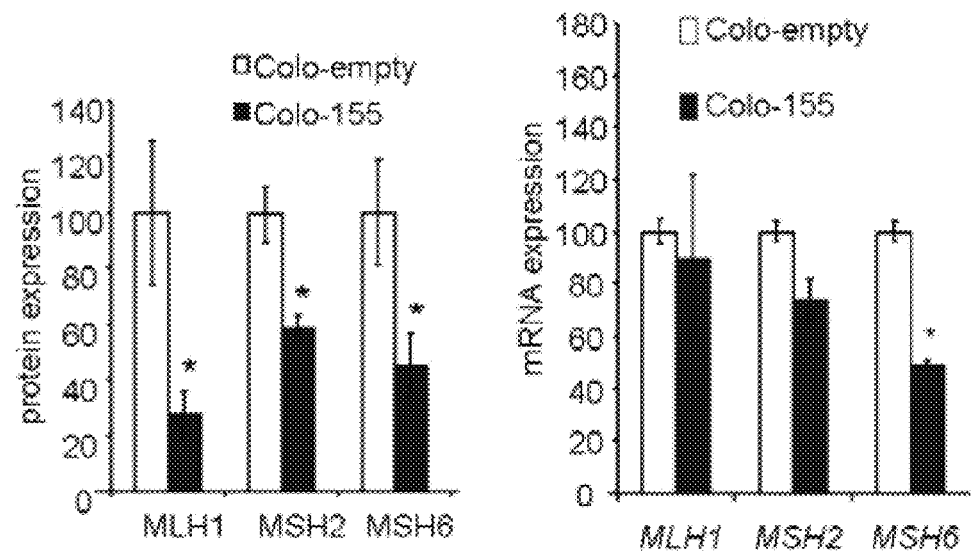

To assess the biological role of miR-155 on MMR regulation, the inventors used a lentiviral vector system to generated stable clones of the Colo-320 DM CRC cells that over-express miR-155 (FIG. 3). The inventors found that MLH1, MSH2 and MSH6 protein expression was reduced by 72%, 42% and 69%, respectively, in Colo-155 DM cells in over-expressing miR-155 (Colo-155) compared to cells expressing an empty vector (Colo-empty; FIG. 3B). The inventors also observed a reduction in MSH6 mRNA (FIG. 3C). Since a direct effect on transcription is unlikely, these results show that miR-155 may target other regulatory factors that affect transcription from the MSH6 promoter.

Figure 3D:
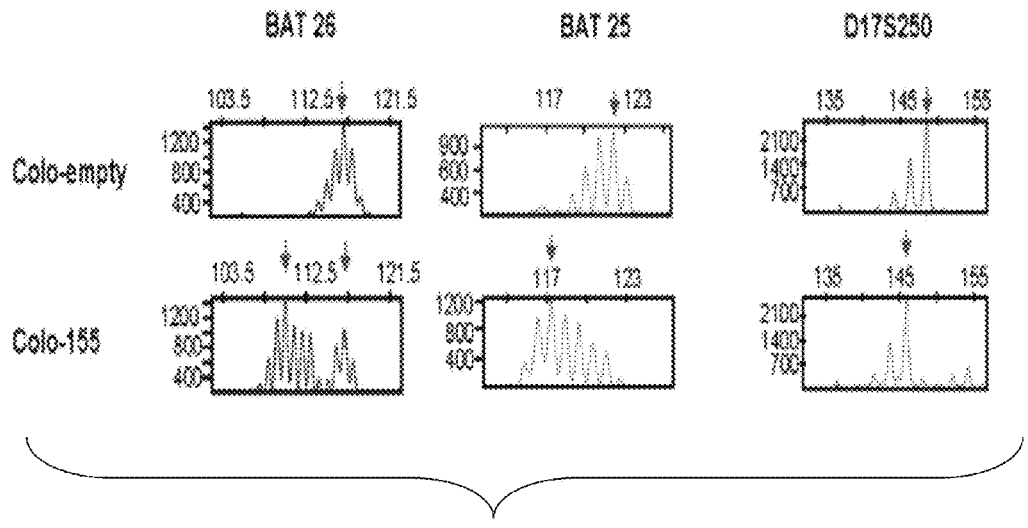
Figure 4A:
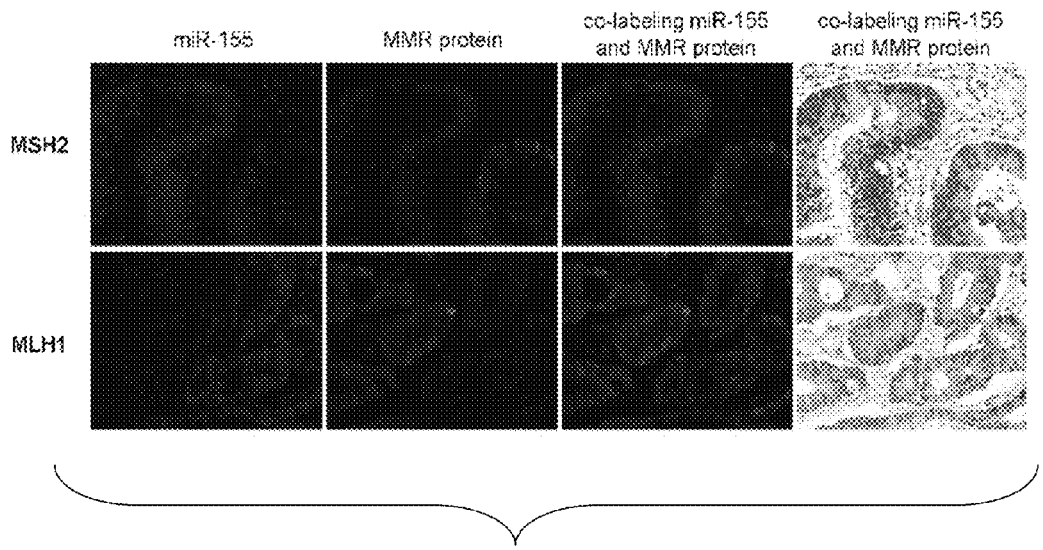
FIGS. 4A-4B: miR-155 expression is inversely related to MLH1 and MSH2 in CRC tissues.
Figure 4B:
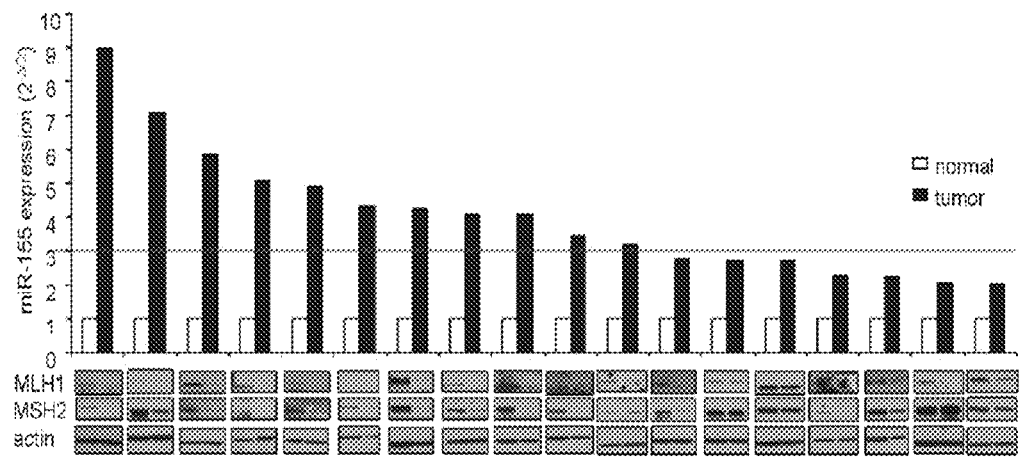

Length changes in simple repeat sequences (microsatellite instability or MSI) are a diagnostic indicator of MMR defects. The inventors examined MSI in the Colo-320 DM over-expressing miR-155 (FIG. 3D). All three of the diagnostic examined (FIG. 3D). These results show that miR-155 over-expression induces replication errors consistent with reduced or absent core MMR functions Example 5 miR-155 Expression Inversely Correlates with hMLH1 and hMSH2 in CRC Tissues

Figure 9A:
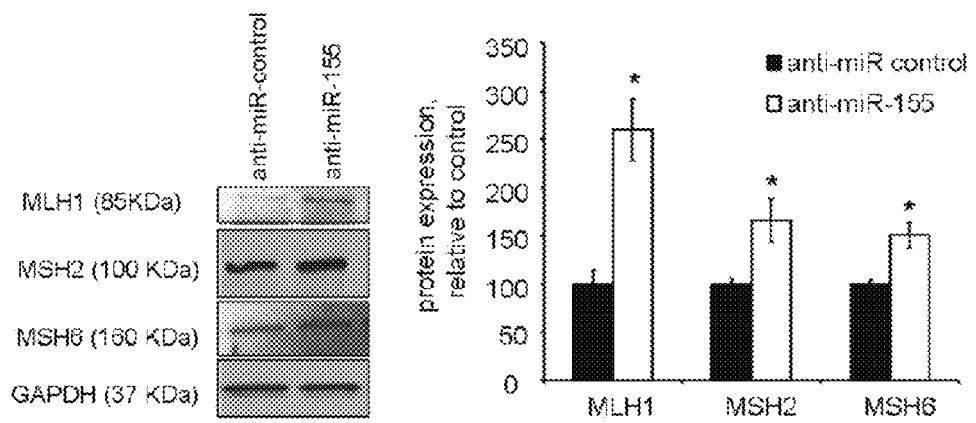
FIGS. 9A 9D: miR-155 and MMR proteins expression in CRC tissues.
Figure 9A:

The inventors examined the expression of miR-155, MLH1 and MSH2 in a tissue microarray containing 70 unselected cases of CRC and 5 benign intestinal lesions. A co-labeling method was used in which the LNA anti-miR-155 or nonspecific LNA anti-miR control was combined with immunohistochemical (IHC) antibodies to hMLH1 or hMSH2. The miR-155 and MMR protein expression was scored positive when detected in >15% or >5% of cells, respectively (FIG. 9A and FIG. 9B).

Figures 9B, 9C:
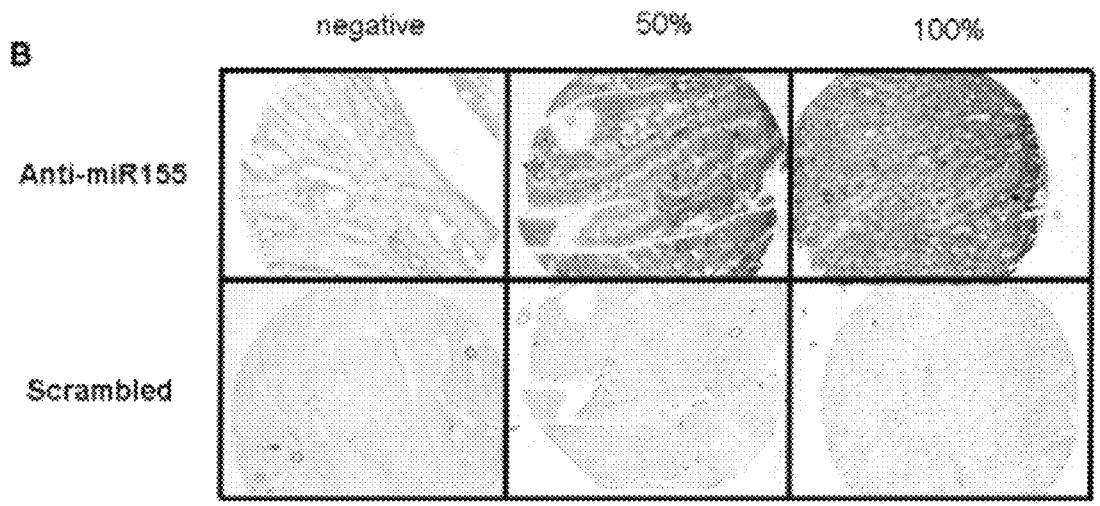
FIG. 9B: Paraffin-embedded, formalin-fixed CRC tissues were incubated with LNA-probe anti-miR-155 or scrambled probe and IHC antibodies against MSH2 and MLH1. miR-155 expression was scored based on the percentage of cells with detectable expression. Representation of 3 different cores stained with LNA anti-miR-155 or LNA scrambled probe. miR-155 and MMR proteins were scored positive when detected in >15% and >5% of cells respectively.
FIG. 9C: Summary data of the proportion of cases with positive or negative staining for miR-155 and MLH1 or MSH2 are shown.

Greater than 50% of the CRCs showed elevated expression of miR-155 (FIG. 9C). Reduction in hMSH2 and hMLH1 expression was observed in 28% and 22% of the CRCs, respectively (FIG. 9C). Co-expression of miR-155 with MSH2 or MLH1 showed an inverse correlation with an r-value of −0.74 for MSH2 (p<0.001) and −0.6 for MLH1 (p<0.001). miR-155 was not co-expressed with hMSH2 in 67% of the CRC tissues and with hMLH1 in 50% of the CRC tissues. When the analysis was conducted with miR-155 positive CRC tissues only, a significant inverse correlation was still evident for both hMLH1 (p=0.0003) and hMSH2 (p=0.001). In the subgroup of tissues with miR-155 expression greater than 50%, there was still an inverse correlation with an r-value of −0.7 for MSH2 (p<0.0002) and −0.55 for MLH1 (p<0.005). Interestingly, in the CRC tissues that were positive for miR-155 and either hMSH2 or hMLH1, a co-expression in the same cancer nest was never observed (FIG. 9C).

Figure 9D:
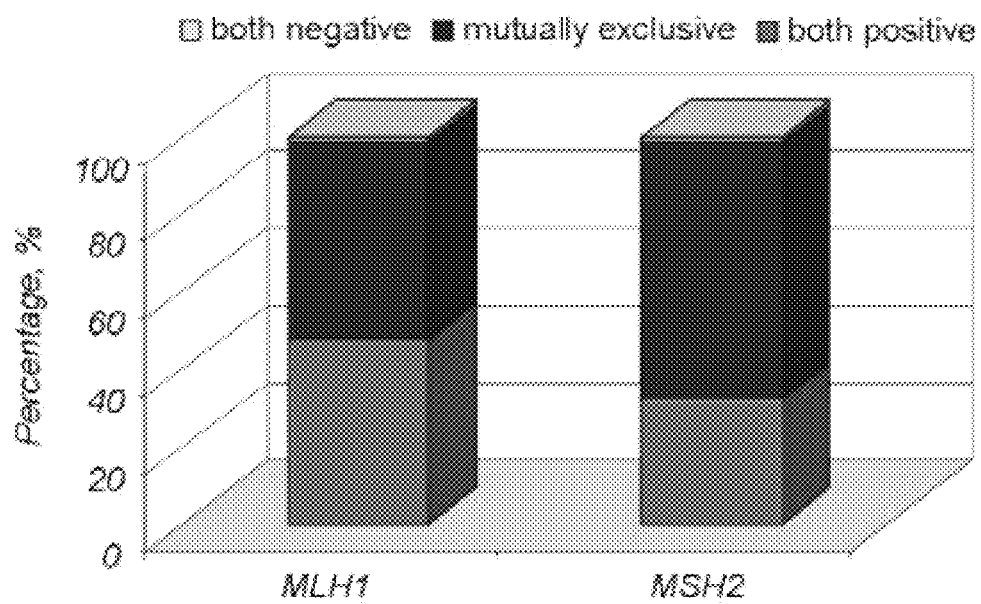

The inventors examined miR-155 and MMR protein expression in a cohort of 83 fresh frozen tumors for which cancer and normal adjacent tissues were available (FIGS. 9C-9D). The inventors examined tumor and associated normal tissue by qPCR analysis and found that the expression of miR-155 was increased by more than 2-fold in 18 (22%) of the specimens. The expression of hMLH1 and MSH2 protein was determined by Western blot analysis in the tumor and associated normal tissue for 18 of these samples. A clear decrease in hMLH1 expression was observed in 12 (67%), while a clear decrease in hMSH2 expression was observed in 11 (61%) of the specimens (FIGS. 9C-9D).

A threshold of uncertain effects on MMR expression appeared to occur when the miR-155 expression level dropped below a 3-fold increase compared to the associated normal tissue (FIGS. 9C-9D). In general, miR-155 expression above this threshold appeared to down-regulate the expression of both hMLH1 and hMSH2. Taken together with the tissue array studies, these results strongly show that miR-155 over-expression in human tumors results in down-regulation of the core MMR proteins hMLH1 and hMSH2.

Example 6 miR-155 Expression as a Cause of MMR Dysregulation in MSI Tumors

MSI is acquired after the inactivation of both alleles of one of the core MMR genes. In LS/HNPCC carriers the majority of mutations are found in the hMSH2 and hMLH1 genes. The "second hit" that leads to an MSI tumor in LS/HNPCC patients is largely the result of loss-of-heterozygosity (LOH) or somatic mutation of the unaffected allele. In CRC, LS/HNPCC accounts for 2-5% of the MSI tumors. Approximately 10-15% of sporadic CRC tumors display MSI that is largely (90%) a result of bi-allelic inactivation of the hMLH1 promoter. In an unselected series of 1066 CRC patients, 135 (12.7%) were found to display MSI. Of these, 23 (5.9%) were determined to have germline mutation in one of the core MMR genes and 106 (78.5%) were found to contain methylation of the hMLH1 promoter. Approximately 5% of these MSI tumors displayed loss-of-expression of at least one of the core MMR proteins with no clear genetic or epigenetic cause.

The inventors have retrospectively examined a series of 40 CRC tumors that displayed MSI and IHC loss-of-expression of at least hMLH1 and hPMS2. Thirty-four of these CRC tumors were found to have mutations in the hMLH1 gene sequence or methylation of the hMLH1 promoter. The inventors examined 6 specimens that retained sufficient sample for miR-155 expression analysis by qPCR following Laser Capture Microdissection of tumor and adjacent normal tissue (Table 1).

Figures 5A, 5B:
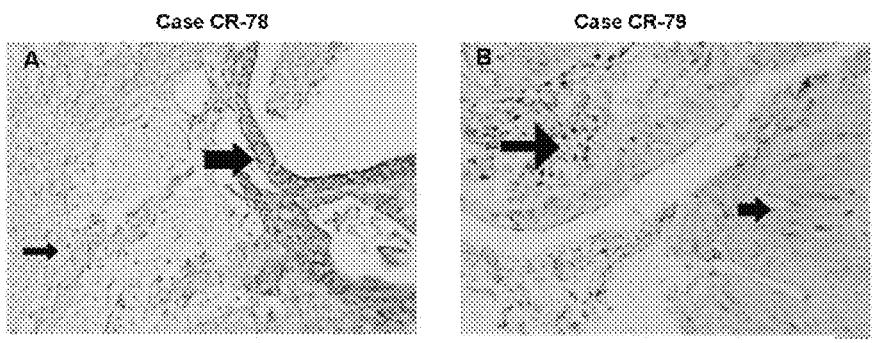
FIGS. 5A-5B: miR-155 expression in hMLH1 negative tumors. miR-155 expression was assessed by in situ hybridization on paraffin-embedded tissues.
Figure 6A:
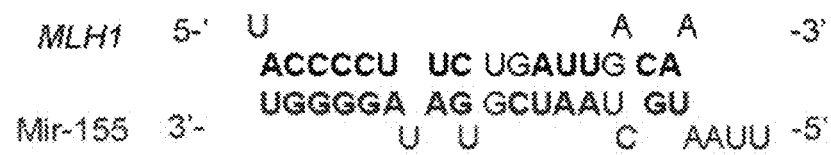
FIGS. 6A-6C: Predicted binding sites of miR-155. Predicted binding sites of miR-155 in MLH1 (SEQ ID NOS 21-22, 23 and 22, respectively, in order of appearance) (FIG. 6A), MSH2 (SEQ ID NOS 24 and 22, respectively, in order of appearance) (FIG. 6B) and MSH6 (SEQ ID NOS 25 and 22, respectively, in order of appearance) (FIG. 6C) genes are illustrated.
Figure 6A:
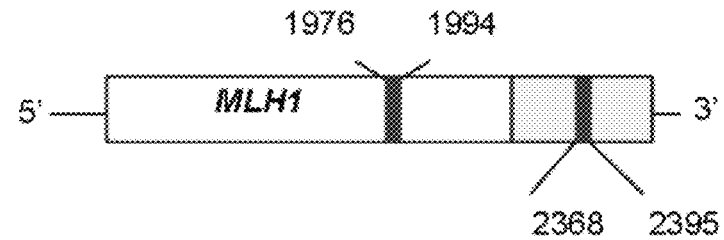
Figure 6A:
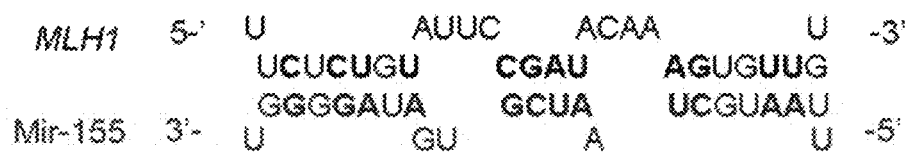
Figure 6B:
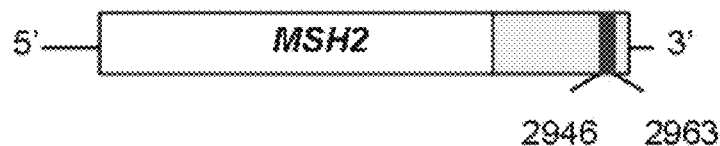
Figure 6B:
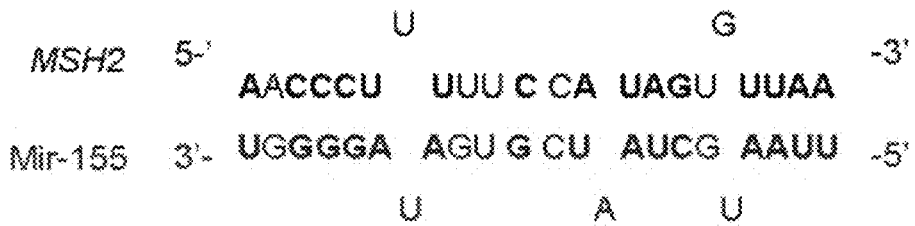
Figure 6C:
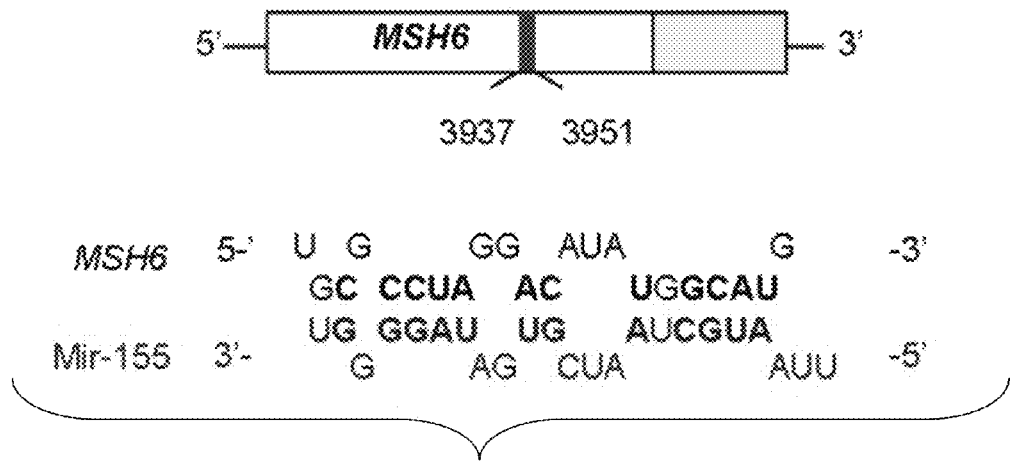

Because one specimen contained very little tissue, the inventors examined miR-155 and hMLH1 expression by in situ and IHC analysis (FIG. 5). All six of the remaining MSI tumors displayed at least a 2-fold increase in miR-155 expression compared to adjacent normal tissue (Table 1), Over-expression of miR-155 in these specimens did not correlate with tumor grade or stage. Three of the samples had an increase of miR-155 over the 3-fold threshold that generally results in reduced expression of hMLH1 and/or hMSH2. In addition, CR78 showed elevated expression of miR-155 in >50% of the tumor tissue and corresponding loss-of-expression of hMLH1 (FIG. 5A and FIG. 5B). These results are consistent with the conclusion that MSI tumors with unknown MMR defects may result from miR-155 over-expression.

TABLE 1

| Sample ID | Age | Sex | Histotype | Tumor Site | TNM | Stage | Grade | miR-155 (fold change: N/T) |
|---|---|---|---|---|---|---|---|---|
| CR04 | 60 | F | adeno | proximal | T2N0M0 | I | LOW | 4.36 |
| CR05 | 86 | M | adeno | proximal | T3N2M0 | III | HIGH | 2.75 |
| CR08 | 66 | M | medullary | proximal | T1N0M0 | I | HIGH | 3.81 |
| CR09 | 83 | M | mucoid | proximal | T3N0M0 | II | HIGH | 2.45 |
| CR12 | 83 | F | tub-muc | proximal | T2N0M0 | I | HIGH | 3.67 |
| CR14 | 67 | F | tub-muc | proximal | T2N0M0 | I | LOW | 2.56 |
| CR78 | 80 | M | adeno | proximal | T3N2M0 | III | HIGH | >50% by ISH |

Table 1: Characteristics of the MSI-H, MLH1/PMS2 mutation negative and MLH1 promoter methylation negative CRC. Clinical-Pathological characteristics: Adeno=adenocarcinoma NAS; tub-muc=adenocarcinoma with mucinous component <50%; Muc=mucinous adenocarcinoma mucinous component >50%; medullary=medullary adenocarcinoma. MiR-155 fold change calculated as ratio of miR-155 expression in tumoral versus adjacent normal tissue after material collection by Laser Capture Microdissection.

TABLE 2

| List of primers used for cloning | | |
|---|---|---|
| Primer Name | Primer Fw 5'-3' | Primer Rv 5'-3' |
| hMLH1 WT | GGAACCTGATTGGATTACCC (SEQ ID NO: 1) | TTATAATCAATCCACTGTGTATAAAGG (SEQ ID NO: 2) |
| hMLH1 MUT-155 CDS | GAGGTGAATTGGGACGAAGA (SEQ ID NO: 3) | TTATAATCAATCCACTGTGTATAAAGG (SEQ ID NO: 4) |

TABLE 2-continued

List of primers used for cloning

| Primer Name | Primer Fw 5'-3' | Primer Rv 5'-3' |
|---|---|---|
| hMLH1 MUT-155 3'-UTR | GCACTGTGGGATGTGTTC TTCTTTATCAAAGTGTG (SEQ ID NO: 5) | CACACTTTGATAAAGAAG AACACATCCCACAGTGC (SEQ ID NO: 6) |
| hMLH1 MUT-155 both sites | GAGGTGAATTGG GACGAAGA (SEQ ID NO: 7) | TTATAATCAATCCA CTGTGTATAAAGG (SEQ ID NO: 8) |
| hMSH2 WT | CAGAAAGCCCTGG AACTTGA (SEQ ID NO: 9) | TCAATTGCAAAC AGTCCTCAG (SEQ ID NO: 10) |
| hMSH2 MUT-155 3'-UTR | ATATTGTTTTATATTCT GTCAGTGCCCATGGGC (SEQ ID NO: 11) | GCCCATGGGCACTGAC AGAATATAAAACAATAT (SEQ ID NO: 12) |
| hMSH6 WT | AAATGTTGCTGTG CGCCTA (SEQ ID NO: 13) | CCACCTTTGTCA GAAGTCAACTC (SEQ ID NO: 14) |
| hMSH6 MUT-155 CDS | GCTTGCTAATCTC CCAGAGG (SEQ ID NO: 15) | CCACCTTTGTCAG AAGTCAACTC (SEQ ID NO: 16) |
| MLH1 MUT CDS | GGAAGGGAACCTGATTG GATCTATGTGCCCCCT TTGGAGGG (SEQ ID NO: 17) | CCCTCCAAAGGGGG CACATAGATCCAAT CAGGTTCCCTTCC (SEQ ID NO: 18) |
| MSH6 MUT CDS | CTCAAAATGTTGCTGT GGCATGCATGGTAG (SEQ ID NO: 19) | CTACCATGCATGCCA CAGCAACATTTTGAG (SEQ ID NO: 20) |

Example 7

Therapeutic/Prophylactic Methods and Compositions

The invention provides methods of treatment and prophylaxis by administration to a subject an effective amount of a therapeutic, i.e., a monoclonal (or polyclonal) antibody, viral vector, Tcl1 mimic or Tcl1 antagonist of the present invention. In a preferred aspect, the therapeutic is substantially purified. The subject is preferably an animal, including but not limited to, animals such as cows, pigs, chickens, etc., and is preferably a mammal, and most preferably human.

Various delivery systems are known and are used to administer a therapeutic of the invention, e.g., encapsulation in liposomes, microparticles, microcapsules, expression by recombinant cells, receptor-mediated endocytosis, construction of a therapeutic nucleic acid as part of a retroviral or other vector, etc. Methods of introduction include, but are not limited to, intradermal, intramuscular, intraperitoneal, intravenous, subcutaneous, intranasal, and oral routes. The compounds are administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir.

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, the implant being of a porous, non-porous, or gelatinous material, including membranes, such as sialastic membranes, or fibers. In one embodiment, administration is by direct injection at the site (or former site) of a malignant tumor or neoplastic or pre-neoplastic tissue.

In a specific embodiment where the therapeutic is a nucleic acid encoding a protein therapeutic the nucleic acid is administered in vivo to promote expression of its encoded protein, by constructing it as part of an appropriate nucleic acid expression vector and administering it so that it becomes intracellular, or coating with lipids or cell-surface receptors or transfecting agents, or by administering it in linkage to a homeobox-like peptide which is known to enter the nucleus. Alternatively, a nucleic acid therapeutic can be introduced intracellularly and incorporated within host cell DNA for expression, by homologous recombination.

The present invention also provides pharmaceutical compositions. Such compositions comprise a therapeutically effective amount of a therapeutic, and a pharmaceutically acceptable carrier or excipient. Such a carrier includes, but is not limited to, saline, buffered saline, dextrose, water, glycerol, ethanol, and combinations thereof. The carrier and composition can be sterile. The formulation will suit the mode of administration.

The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition also includes a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it is be dispensed with an infusion bottle containing sterile pharmaceutical grade water or saline. Where the composition is administered by injection, an ampoule of sterile water for injection or saline is provided so that the ingredients are mixed prior to administration.

The therapeutics of the invention are formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the therapeutic of the invention which will be effective in the treatment of a particular disorder or condition will depend on the nature of the disorder or condition, and is determined by standard clinical techniques. In addition, in vitro assays may optionally be employed to help identify optimal dosage ranges. The precise dose to be employed in the formulation will also depend on the route of administration, and the seriousness of the disease or disorder, and is decided according to the judgment of the practitioner and each patient's circumstances. However, suitable dosage ranges for intravenous administration are generally about 20-500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems The invention also provides a pharmaceutical pack or kit comprising one or more containers filled with one or more of the ingredients of the pharmaceutical compositions of the invention. Optionally associated with such container(s) is a notice in the form prescribed by a governmental agency regulating the manufacture, use or sale of pharmaceuticals or biological products, which notice reflects approval by the agency of manufacture, use or sale for human administration.

Example 8

Method of Treating Cancer Patients

This example describes a method of selecting and treating patients that are likely to have a favorable response to treatments with compositions herein.

A patient diagnosed with cancer ordinarily first undergoes tissue resection with an intent to cure. Tumor samples are obtained from the portion of the tissue removed from the patient. RNA is then isolated from the tissue samples using any appropriate method for extraction of small RNAs that are well known in the art, such as by using TRIZOL™. Purified RNA is then subjected to RT-PCR using primers specific miR-21 or other differentially expressed miRNAs disclosed, optionally in conjunction with genetic analysis. These assays are run to determine the expression level of the pertinent RNA in the tumor. If differentially expressed miR expression pattern is determined, especially if mutant status is ascertained, the patient is a candidate for treatment with the compositions herein.

Accordingly, the patient is treated with a therapeutically effective amount of the compositions according to methods known in the art. The dose and dosing regimen of the compositions will vary depending on a variety of factors, such as health status of the patient and the stage of the cancer. Typically, treatment is administered in many doses over time.

Example 9

Methods of Diagnosing Cancer Patients

In one particular aspect, there is provided herein a method of diagnosing whether a subject has, or is at risk for developing, cancer. The method generally includes measuring the differential miR expression pattern of the miR-155 compared to control. If a differential miR expression pattern is ascertained, the results are indicative of the subject either having, or being at risk for developing, cancer. In certain embodiments, the level of the at least one gene product is measured using Northern blot analysis. Also, in certain embodiments, the level of the at least one gene product in the test sample is less than the level of the corresponding miR gene product in the control sample, and/or the level of the at least one miR gene product in the test sample is greater than the level of the corresponding miR gene product in the control sample.

Example 10

Measuring miR Gene Products

The level of the at least one miR gene product can be measured by reverse transcribing RNA from a test sample obtained from the subject to provide a set of target oligodeoxynucleotides; hybridizing the target oligodeoxynucleotides to a microarray comprising miRNA-specific probe oligonucleotides to provide a hybridization profile for the test sample; and, comparing the test sample hybridization profile to a hybridization profile generated from a control sample. An alteration in the signal of at least one miRNA is indicative of the subject either having, or being at risk for developing, lung cancer, particularly EGFR mutant lung cancer.

Example 11

Diagnostic and Therapeutic Applications

In another aspect, there is provided herein are methods of treating a cancer in a subject, where the signal of at least one miRNA, relative to the signal generated from the control sample, is de-regulated (e.g., down-regulated and/or up-regulated).

Also provided herein are methods of diagnosing whether a subject has, or is at risk for developing, a cancer associated with one or more adverse prognostic markers in a subject, by reverse transcribing RNA from a test sample obtained from the subject to provide a set of target oligodeoxynucleotides; hybridizing the target oligodeoxynucleotides to a microarray comprising miRNA-specific probe oligonucleotides to provide a hybridization profile for the test sample; and, comparing the test sample hybridization profile to a hybridization profile generated from a control sample. An alteration in the signal is indicative of the subject either having, or being at risk for developing, the cancer.

Example 12

Kits

Any of the compositions described herein may be comprised in a kit. In a non-limiting example, reagents for isolating miRNA, labeling miRNA, and/or evaluating an miRNA population using an array are included in a kit. The kit may further include reagents for creating or synthesizing miRNA probes. The kits will thus comprise, in suitable container means, an enzyme for labeling the miRNA by incorporating labeled nucleotide or unlabeled nucleotides that are subsequently labeled. It may also include one or more buffers, such as reaction buffer, labeling buffer, washing buffer, or a hybridization buffer, compounds for preparing the miRNA probes, and components for isolating miRNA. Other kits may include components for making a nucleic acid array comprising oligonucleotides complementary to miRNAs, and thus, may include, for example, a solid support.

For any kit embodiment, including an array, there can be nucleic acid molecules that contain a sequence that is identical or complementary to all or part of any of the sequences herein.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit (labeling reagent and label may be packaged together), the kit also will generally contain a second, third or other additional container into which the additional components may be separately placed. However, various combinations of components may be comprised in a vial. The kits of the present invention also will typically include a means for containing the nucleic acids, and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being one preferred solution. Other solutions that may be included in a kit are those solutions involved in isolating and/or enriching miRNA from a mixed sample.

However, the components of the kit may be provided as dried powder(s). When reagents and/or components are provided as a dry powder, the powder can be reconstituted by the addition of a suitable solvent. It is envisioned that the solvent may also be provided in another container means. The kits may also include components that facilitate isolation of the labeled miRNA. It may also include components that preserve or maintain the miRNA or that protect against its degradation. The components may be RNAse-free or protect against RNAses.

Also, the kits can generally comprise, in suitable means, distinct containers for each individual reagent or solution. The kit can also include instructions for employing the kit components as well the use of any other reagent not included in the kit. Instructions may include variations that can be implemented. It is contemplated that such reagents are embodiments of kits of the invention. Also, the kits are not limited to the particular items identified above and may include any reagent used for the manipulation or characterization of miRNA.

It is also contemplated that any embodiment discussed in the context of an miRNA array may be employed more generally in screening or profiling methods or kits of the invention. In other words, any embodiments describing what may be included in a particular array can be practiced in the context of miRNA profiling more generally and need not involve an array per se.

It is also contemplated that any kit, array or other detection technique or tool, or any method can involve profiling for any of these miRNAs. Also, it is contemplated that any embodiment discussed in the context of an miRNA array can be implemented with or without the array format in methods of the invention; in other words, any miRNA in an miRNA array may be screened or evaluated in any method of the invention according to any techniques known to those of skill in the art. The array format is not required for the screening and diagnostic methods to be implemented.

The kits for using miRNA arrays for therapeutic, prognostic, or diagnostic applications and such uses are contemplated by the inventors herein. The kits can include an miRNA array, as well as information regarding a standard or normalized miRNA profile for the miRNAs on the array. Also, in certain embodiments, control RNA or DNA can be included in the kit. The control RNA can be miRNA that can be used as a positive control for labeling and/or array analysis.

The methods and kits of the current teachings have been described broadly and generically herein. Each of the narrower species and sub-generic groupings falling within the generic disclosure also form part of the current teachings. This includes the generic description of the current teachings with a proviso or negative limitation removing any subject matter from the genus, regardless of whether or not the excised material is specifically recited herein.

Example 13

Array Preparation and Screening

Also provided herein are the preparation and use of miRNA arrays, which are ordered macroarrays or microarrays of nucleic acid molecules (probes) that are fully or nearly complementary or identical to a plurality of miRNA molecules or precursor miRNA molecules and that are positioned on a support material in a spatially separated organization. Macroarrays are typically sheets of nitrocellulose or nylon upon which probes have been spotted. Microarrays position the nucleic acid probes more densely such that up to 10,000 nucleic acid molecules can be fit into a region typically 1 to 4 square centimeters.

Microarrays can be fabricated by spotting nucleic acid molecules, e.g., genes, oligonucleotides, etc., onto substrates or fabricating oligonucleotide sequences in situ on a substrate. Spotted or fabricated nucleic acid molecules can be applied in a high density matrix pattern of up to about 30 non-identical nucleic acid molecules per square centimeter or higher, e.g. up to about 100 or even 1000 per square centimeter. Microarrays typically use coated glass as the solid support, in contrast to the nitrocellulose-based material of filter arrays. By having an ordered array of miRNA-complementing nucleic acid samples, the position of each sample can be tracked and linked to the original sample.

A variety of different array devices in which a plurality of distinct nucleic acid probes are stably associated with the surface of a solid support are known to those of skill in the art. Useful substrates for arrays include nylon, glass and silicon. The arrays may vary in a number of different ways, including average probe length, sequence or types of probes, nature of bond between the probe and the array surface, e.g. covalent or non-covalent, and the like. The labeling and screening methods described herein and the arrays are not limited in its utility with respect to any parameter except that the probes detect miRNA; consequently, methods and compositions may be used with a variety of different types of miRNA arrays.

In view of the many possible embodiments to which the principles of the inventors' invention may be applied, it should be recognized that the illustrated embodiments are only preferred examples of the invention and should not be taken as a limitation on the scope of the invention. Rather, the scope of the invention is defined by the following claims. The inventors therefore claim as the inventors' invention all that comes within the scope and spirit of these claims.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof. Therefore, it is intended that the invention not be limited to the particular embodiment disclosed herein contemplated for carrying out this invention, but that the invention will include all embodiments falling within the scope of the claims.

What is claimed is:

1. A method for restoring a desired expression of at least one core mismatch repair (MMR) protein in a cell in need thereof, comprising administering to the cell an effective amount of at least anti-miR-155 in an amount sufficient to increase expression of one or more core MMR proteins selected from: human MutS homolog 2 (MSH2), human MutS homolog 6 (MSH6), and human MutL homolog 1 (MLH1).

2. The method of claim 1, wherein the cell is a cancer cell.

3. The method of claim 2, wherein the cancer is colorectal cancer.

4. The method of claim 1, wherein the anti-miR-155 comprises a locked nucleic acid modified oligonucleotide that targets miR-155.

5. The method of claim 1, wherein the cell is in a human subject.

6. A method for inducing re-expression of at least one mismatch repair MMR gene in a cell in need thereof, comprising administering to the cell an effective amount of an anti-miR-155 sufficient to induce MMR gene expression selected from one or more of human MutS homolog 2 (MSH2), human MutS homolog 6 (MSH6), and human MutL homolog 1 (MLH1).

7. The method of claim 6, wherein the cell is a cancer cell.

8. The method of claim 7, wherein the cancer is colorectal cancer.

9. The method of claim 6, wherein the anti-miR-155 comprises a locked nucleic acid modified oligonucleotide that targets miR-155.

10. The method of claim 6, wherein the cell is in a human subject.

11. A method for increasing expression of a mismatch repair (MMR) protein in a cell in need thereof, the method comprising: transfecting a cell with an anti-miR-155 nucleic acid construct in an amount sufficient to increase expression of one or more MMR proteins selected from: human MutS homolog 2 (MSH2), human MutS homolog 6 (MSH6), and human MutL homolog 1 (MLH1).

12. The method of claim 11, wherein the cell is a cancer cell.

13. The method of claim 12, wherein the cancer is colorectal cancer.

14. The method of claim 11, wherein the anti-miR-155 nucleic acid construct comprises a locked nucleic acid modified oligonucleotide that targets miR-155.

15. The method of claim 11, wherein the cell is in a human subject.

16. A method of up-regulating at least one mismatch repair (MMR) gene in a cell, comprising introducing into the cell an effective amount of a miR-specific inhibitor of at least miR-155 into the cell sufficient to alter expression patterns of one or more proteins encoded by the MMR gene, the mismatch repair (MMR) proteins being selected from: human MutS homolog 2 (MSH2), human MutS homolog 6 (MSH6), and human MutL homolog 1 (MLH1).

17. The method of claim 16, wherein the cell is a cancer cell.

18. The method of claim 17, wherein the cancer is colorectal cancer.

19. The method of claim 16, wherein the miR-specific inhibitor is anti-sense miR-155.

20. The method of claim 19, wherein the anti-sense miR-155 comprises a locked nucleic acid modified oligonucleotide that targets miR-155.

21. The method of claim 16, wherein the cell is in a human subject.

* * * * *